US007893094B2

(12) United States Patent
Pollard et al.

(10) Patent No.: US 7,893,094 B2
(45) Date of Patent: Feb. 22, 2011

(54) AMPHIPHILIC PYRIDINIUM COMPOUNDS, METHOD OF MAKING AND USE THEREOF

(75) Inventors: Harvey B. Pollard, Potomac, MD (US); Kenneth Jacobson, Silver Spring, MD (US)

(73) Assignees: The Henry M. Jackson Foundation for the Advancement of Military Medicine, Inc., Rockville, MD (US); National Institutes of Health (NIH), Bethesda, MD (US)

( * ) Notice: Subject to any disclaimer, the term of this patent is extended or adjusted under 35 U.S.C. 154(b) by 1072 days.

(21) Appl. No.: 10/560,590

(22) PCT Filed: Jun. 28, 2004

(86) PCT No.: PCT/US2004/020718

§ 371 (c)(1),
(2), (4) Date: Jun. 27, 2006

(87) PCT Pub. No.: WO2005/002519

PCT Pub. Date: Jan. 13, 2005

(65) Prior Publication Data

US 2007/0105916 A1    May 10, 2007

Related U.S. Application Data

(60) Provisional application No. 60/482,764, filed on Jun. 27, 2003.

(51) Int. Cl.
*A61K 31/4425* (2006.01)
*C07D 213/20* (2006.01)
*C07D 213/30* (2006.01)

(52) U.S. Cl. .................. 514/358; 546/316; 546/335; 546/342

(58) Field of Classification Search ............... 546/316, 546/335, 342; 514/358
See application file for complete search history.

(56) References Cited

U.S. PATENT DOCUMENTS 6,500,852 B1    12/2002    Brouillette et al.

FOREIGN PATENT DOCUMENTS

| WO | 02/065977 A2 | 8/2002 |
|---|---|---|
| WO | WO 02/065977 A2 | 8/2002 |

OTHER PUBLICATIONS

International Search Report and Written Opinion issued Jul. 12, 2005 in corresponding PCT/US04/20718.
R. Betz, et al. "Increased Sputum IL-8 and IL-5 in Asymptomatic Nonspecific Airway Hyperresponsiveness", Lung 179:119-133, Springer-Verlag, New York (2001).
J.C.M. Morel, et al. "Interleukin-18 Induces Rheumatoid Arthritis Synovial Fibroblast CXC Chemokine Production through NFκB Activation", Laboratory Investigation, p. 1371, vol. 81, No. 10, Chicago, Illinois (2001).
K. Hayashida, et al. "Synovial stromal cells from rheumatoid arthritis patients attract monocytes by producing MCP-1 and IL-8", Arthritis Research, arthritis-research.com., p. 118-126, vol. 3, No. 2 (2001).
M. C. Kraan, et al. "The development of clinical signs of rheumatoid synovial inflammation is associated with increased synthesis of the chemokine CXCL8 (interleukin-8)", Arthritis Research, arthritis-research.com., p. 65-71, vol. 3, No. 1 (2000).
Nandate, K., et al. "Cerebrovascular Cytokine Responses During Coronary Artery Bypass Surgery: Specific Production of Interleukin-8 and Its Attenuation by Hypothermic Cardiopulmonary Bypass", Anesthesia Analogue. p. 823-828, vol. 89, United Kingdom (1999).
E. Dimango, et al, "*Pseudomonas aeruginosa* Gene Products Stimulate Respiratory Epithelial Cells to Produce Interleukin-8", The American Society for Clinical Investigation, Inc., p. 2204-2210 vol. 96, (1995).
T. Ito, et al., "Significance of Elevated Serum Interleukin-8 in Patients Resuscitated After Cardiopulmonary Arrest" Rususcitation, pp. 47-53, vol. 51, Elsevier Science Ireland, Ltd. (2001).
J. A. Iocono, MD., "Interleukin-8 Levels and Activity in Delayed-Healing Human Thermal Wounds", Wound Repair and Regeneration, pp. 216-225, vol. 8, No. 3, The Wound Healing Society (2000).
A. Imada, et al., "Coordinate Upregulation of Interleukin-8 and Growth-Related Gene Product -σ is Present in the Colonic Mucosa of Inflammatory Bowel Disease", pp. 854-864, vol. 8, Scan J. Gastroenterol. (2001).
I.K. Gao, et al., "Inhibition of Interleukin-8 Synthesis by Intraarticular Methotrexate Therapy in Patientes with Rheumatoid Arthritis", Zeitschrift für Rheumatologie, pp. 95-100, vol. 57, No. 2, Steinkopff, Verlag, Germany (1998).
G. Goping, et al., "Effect of MPTP on Dopaminergic Neurons in the Goldfish Brain: A Light and Electron Microscope Study", Brain Research, pp. 35-52, vol. 687, Elsevier Science (1995).
N. Drabe, et al., "Genetic Predisposition in Patients Undergoing Cardiopulmonary Bypass Surgery Is Associated With an Increase of Inflammatory Cytokines", European Journal of Cardio-thoracic Surgery, pp. 609-613, vol. 20, Elsevier, Science (2001).
S.G. Muehlstedt, MD., "Cytokines and the Pathogenesis of Nosocomial Pneumonia", Surgery, pp. 602-611, vol. 130, No. 4., Mosby, Inc. (2001).
N. Arispe, et al., "Alzheimer Disease Amyloid β Protein Forms Calcium Channels in Bilayer Membranes: Blockage by Tromethamine and Aluminum", pp. 567-57, vol. 90, Proc. National Academy of Sciences, USA. (1993).
N. Arispe, et al., "Intrinsic Anion Channel Activity of the Recombinant First Nucleotide Binding Fold Domain of the Cystic Fibrosis Transmembrane Regulatory Protein", pp. 1539-1543, vol. 89. Proc. National Academy of Sciences, USA (1992).

(Continued)

*Primary Examiner*—Patricia L Morris
(74) *Attorney, Agent, or Firm*—Buchanan Ingersoll & Rooney PC

(57) ABSTRACT

The present invention is directed to the amphiphilic pyridinium compounds, such as for suppressing IL-8 secretion and production. The present invention further provides methods of making and using such compounds for the treatment of the IL-8 related diseases, such as cystic fibrosis.

14 Claims, 2 Drawing Sheets

OTHER PUBLICATIONS

D. Armstrong, et al., "Lower Airway Inflammation in Infants and Young Children with Cystic Fibrosis", pp. 1197-1204, vol. 156, American Journal of Respiratory Critical Care Medicine, USA. (1997).

A. J. Fisher, et al., Elevated Levels of Interleukin-8 in Donor Lungs Is Associated with Early Graft Failure after Lung Transplantation, pp. 259-265, vol. 163, American Journal of Respiratory and Critical Care Medicine., USA (2001).

M. Laffon, et al, "Interleukin-8 Mediates Injury from Smoke Inhalation to Both the Lung Endothelial and the Alveolar Epithelial Barriers in Rabbits", pp. 1443-1449, vol. 160, American Journal of Respiratory and Critical Care Medicine, USA (1999).

K. Modelsak, et al., "Acid-induced Lung Injury", pp. 1450-1456, vol. 160, American Journal of Respiratory and Critical Care Medicine, USA. (1999).

M. Nakamura, et al., Importance of Interleukin-8 in the Development of Reexpansion Lung Injury in Rabbits, pp. 1030-1036, vol. 161, American Journal of Respiratory and Critical Care Medicine, USA (2000).

P.S. Gilmour, et al., Adenoviral E1A Primes Alveolar Epithelial Cells to $PM_{10}$-induced Transcription of Interleukin-8, pp. L598-L606, vol. 281, American Journal of Physiology—Lung Cell Mol Physiology, www.ajplung.org (2001).

O. Tabary, et al., "Selective Up-Regulation of Chemokine IL-8 Expression in Cystic Fibrosis Bronchial Gland Cells in Vivo and in Vitro" American Journal of Pathology, pp. 921-930, vol. 153, No. 3, American Society for Investigative Pathology, USA.(1998).

A.S. Baldwin, Jr., et al. "The NF-κB and IκB Proteins: New Discoveries and Insights", The Anatomical Record, Annual Review Immunol pp. 649-681, vol. 14 ,Annual Reviews, Inc. (1996).

H. B. Pollard, et al. Anatomic Genomics: Systems of Genes Supporting the Biology of Systems pp. fmiii-ix, vol. 259, Wiley-Liss, Inc. (2000).

M. Stangl, et al. "Influence of Brain Death on Cytokine Release in Organ Donors and Renal Transplants", Transplantation Proceedings, pp. 1284-1285, vol. 33, Elsevier Science, Inc. (2001).

Y. Takahashi, et al. "The Participation of IL-8 in the Synovial Lesions at an Early Stage of Rheumatoid Arthritis", Tohoku, pp. 75-87, vol. 188, J. Exp. Med. Japan (1999).

A. R. Brasier, et al.,"A Promoter Recruitment Mechanism for Tumor Necrosis Factor -α-induced Interleukin-8 Transcription in Type II Pulmonary Epithelial Cells", The Journal of Biological Chemistry, pp. 3551-3561, vol. 273, No. 6, The American Society for Biochemistry and Molecular Biology, Inc. (1997).

M. Nourbakhsh, et al., "The NF-κB Repressing Factor Is Involved in Basal Repression and Interleukin (IL)-1-induced Activation of IL-8 Transcription by Binding to a Conserved NF-κB-flanking Sequence Element" , The Journal of Biological Chemistry, pp. 4501-4508, vol. 276, No. 6, The American Society for Biochemistry and Molecular Biology, Inc. (2001).

N. Wang, et al., "Interleukin 8 Is Induced by Cholesterol Loading of Macrophages and Expressed by Macrophage Foam Cells in Human Atheroma", The Journal of Biological Chemistry, pp. 8837-8842, vol. 271, No. 15, The American Society for Biochemistry and Molecular Biology, Inc. (1996).

G. D. Wu, et al., "Oct-1 and CCAAT/Enhancer-binding Protein (C/EBP) Bind to Overlapping Elements within the Interleukin-8 Promoter" The Journal of Biological Chemistry, pp. 2396-2403, vol. 272, No. 4, The American Society for Biochemistry and Molecular Biology, Inc. (1996).

A. Casola, et al. "Requirement of a Novel Upstream Response Element in Respiratory Syncytial Virus-Induced IL-8 Gene Expression", The Journal of Immunology, pp. 5944-5951, The American Association of Immunologists. (2000).

B. D. Gitter, et al., Amyloid β Peptide Potentiates Cytokine Secretion by Interleukin-1β-Activated Human Astrocytoma Cells, pp. 10738-10741, vol. 92, Proc. Natl. Academy of Sciences, USA. (1995).

A. E. Koch, et al., "Regulation of Angiogenesis by the C-X-C Chemokines Interleukin-8 and Epithelial Neutrophil Activating Peptide 78 in the Rheumatoid Joint" pp. 31-40, vol. 44, No. 1, American College of Rheumatology. (2001).

PE Lipsky, et al. Rheumatoid Arthritis, pp. 1-25, Harrison's Internal Medicine—Part 13, Section 2, Chapter 301, McGraw-Hill's Access Medicine. (2006).

A. König, et al. "Inflammatory Infiltrate and Interleukin-8 Expression in the Synovium of Psoriatic Arthritis—an Immunohistochemical and mRNA Analysis", pp. 159-168, vol. 17, Rheumatol Int. (1997).

C. Marguet, et al. "Eosinophil Cationic Protein and Interleukin-8 Levels in Bronchial Lavage Fluid From Children With Asthma and Infantile Wheeze", pp. 27-33, vol. 12, Pediatric Allergy and Immunology., United Kingdom (2001).

J. M. Pilewski, et al. "Role of CFTR in Airway Disease", Physiological Reviews, pp. S215-S255, vol. 79, Suppl., No. 1, University of Pittsburgh, Pittsburgh, PA. (1999).

M. Nishimura, et al. "Tumor Necrosis Factor Gene Polymorphisms in Patients With Sporadic Parkinson's Disease", Neuroscience Letters, pp. 1-4, vol. 311, Elsevier Science Ireland, Ltd. (2001).

E. Sherwood, et al., Interleukin-8, Neuroinflammation, and Secondary Brain Injury, Critical Care Medicine, Official Journal of the Society of Critical Care Medicine; pp. 1221-1223, vol. 28(4) Lippincott, Williams & Wilkins. (2000).

M. Whalen, et al. Effect of Neutropenia and Granulocyte Colony Stimulating Factor-Induced Neutrophilia on Blood-Brian Barrier Permeability and Brain Edema After Traumatic Brain Injury in Rats, Neurologic Critical Care, Critical Care Medicine, pp. 3710-3717, vol. 28, No. 11, Official Journal of the Society of Critical Care Medicine. (2000).

M. Whalen, et al. Intercellular Adhesion Molecule-1 and Vascular Cell Adhesion Molecule-1 Are Increased in the Plasma of Children With Sepsis-Induced Multiple Organ Failure, Critical Care Medicine, Official Journal of The Society of Critical Care Medicine pp. 2600-2607, vol. 28, No. 7,. Lippincott, Williams & Wilkins. (2000).

M. Whalen, et al., "Interleukin-8 Is Increased in Cerebrospinal Fluid of Children With Severe Head Injury", pp. 929-934, vol. 28(4), Critical Care Medicine, Official Journal of The Society of Critical Care Medicine, Lippincott, Williams & Wilkins. (2000).

T. Kossmann, et al., "Interleukin-8 Released Into the Cerebrospinal Fluid After Brain Injury Is Associated With Blood-Brain Barrier Dysfunction and Nerve Growth Factor Production", Journal of Cerebral Blood Flow & Metabolism,pp. 280-289, vol. 17, (1997).

E. Tarkowski, et al., "Intrathecal Release of Pro-and Anti-inflammatory Cytokines During Stroke", Clinical and Experimental Immunology, pp. 492-499, vol. 110, Blackwell Science, Ltd. (1997).

M. Subauste, et al. , Effects of Tumor Necrosis Factor -α, Epidermal Growth Factor and Transforming Growth Factor-α on Interleukin-8 Production By, and Human Rhinovirus Replication In, Bronchial Epithelial Cells, International Immunopharmacology, pp. 1229-1234, vol. 1, Elsevier Science, Inc. (2001).

R. Temaru, et al., High Glucose Enhances the Gene Expression of Interleukin-8 in Human Endothelial Cells, But Not in Smooth Muscle Cells: Possible Role of Interleukin-8 in Diabetic Macroangiopathy, Diabetologia, pp. 610-613, vol. 40, Springer-Verlag. (1997).

P. R. Troughton, et al., "Synovial Fluid Interleukin-8 and Neutrophil Function in Rheumatoid Arthritis and Seronegative Polyarthritis", pp. 1244-1251, vol. 35, British Society for Rheumatology (1996).

T. J. Stoof, et al. "The Antipsoriatic Drug Dimethylfumarate Strongly Suppresses Chemokine Production in Human Keratinocytes and Peripheral Blood Mononuclear Cells", pp. 1114-1120, vol. 144, British Journal of Dermatology, British Association of Dermatologists (2001).

B. Stein, et al. "Distinct Mechanisms for Regulation of the Interleukin-8 Gene Involve Synergism and Cooperativity Between C/EBP and NF-κB", Molecular and Cellular Biology, pp. 7191-7198, vol. 13, No. 11, American Society for Microbiology (1993).

H. Vindenes, MD, et al. , Increased Levels of Circulating Interleukin-8 in Patients With Large Burns: Relation to Burn Size and Sepsis, The Journal of Trauma, Injury, Infection and Critical Care, pp. 635-640, vol. 39 (4), The Journal of Trauma, Injury, Infection and Critical Care, Williams & Wilkins.(1995).

Kerem, B, et al., "Identification of the Cystic Fibrosis Gene: Genetic Analysis", 16 pages, American Association for the Advancement of Science (1989).

Riordan, D., et al, Identification of the Cystic Fibrosis Gene: Cloning and Characterization of Complementary DNA, 15 pages, American Association for the Advancement of Science (2006).

Rommens, J., et al., Identification of the Cystic Frbrosis Gene: Chromosome Walking and Jumping, 13 pages, American Association for the Advancement of Science (1989).

Abman, S., et al., Early Bacteriologic, Immunologic, and Clinical Courses of Young Infants With Cystic Fibrosis Identified by Neonatal Screening, pp. 211-217, vol. 119, No. 2, The Journal of Pediatrics. (1991).

S. Höxtermann, et al., "Fumaric Acid Esters Suppress Peripheral CD4- and CD8-Positive Lymphocytes in Psoriasis", Dermatology, pp. 223-230, vol. 196, Karger, Basel, Switzerland (1998).

L. Ott, et al., Cytokines and Metabolic Dysfunction After Severe Head Injury, pp. 447-472, vol. 11, Journal of Neurotrauma (1994).

C. Ruef, et al. "Regulation of Cytokine Secretion by Cystic Fibrosis Airway Epithelial Cells", 1429-1436. vol. 6, European Respiratory Journal, Ltd. (1993).

T. Matsumoto, et al., "Prevention of Cerebral Edema and Infarct in Cerebral Reperfusion Injury by an Antibody to Interleukin-8", p. 119-125, vol. 77, No. 2, Laboratory Investigation. (1997).

T.P. Dean, et al., "Interleukin-8 Concentrations Are Elevated in Bronchoalveolar Lavage, Sputum, and Sera of Children with Cystic Fibrosis", Pediatric Research, pp. 159-161, vol. 34, No. 2, International Pediatric Research Foundation, Inc. (1993).

T.Z. Khan, et al., "Early Pulmonary Inflammation in Infants with Cystic Fibrosis", pp. 1075-1082, vol. 151, American Journal of Respiratory and Critical Care Medicine.(1994).

I. Ertenili, et al. "Synovial Fluid Cytokine Levels in Behcet's Disease", pp. S37-S-41, vol. 19, Clinical and Experimental Rheumatology. (2001).

K. Inoue, et al., "Adenoviral-Mediated Gene Therapy of Human Bladder Cancer With Antisense Interleukin-8", pp. 955-964, vol. 8, Oncology Reports. (2001).

B. Maier, et al., "Differential Release of Interleukines 6, 8, and 10 in Cerebrospinal Fluid and Plasma After Traumatic Brain Injury", pp. 421-426, vol. 15, No. 6, Shock. (2001).

M. Osman, et al., "Graded Experimental Acute Pancreatitis: Monitoring of a Renewed Rabbit Model Focusing on the Production of Interleukin-8 (IL-8) and CD11b/CD18", vol. 11, No. 2, European Journal of Gastroenterology & Hepatology.(1999).

T. Suzuki, et al., Tax Protein of HTLV-1 Interacts With the Rel Homology Domain of NF-κB p65 and C-Rel Proteins Bound to the NF-κB Binding Site and Activates Transcription, pp. 3099-3015, vol. 9, Oncogene. (1994).

J. L. Rodriguez, MD., "Correlation of the Local and Systemic Cytokine Response With Clinical Outcome Following Thermal Injury", pp. 684-695, vol. 34. No. 5, The Journal of Trauma, Williams and Wilkins. (1993).

M. Xia, et al., "Interleukin-8 Receptor B Immunoreactivity in Brain and Neuritic Plaques of Alzheimer's Disease" American Journal of Pathology, pp. 1267-1274, vol. 150, No. 4, American Society for Investigative Pathology (1997).

S. G. Elner, et al., "Cytokines in Proliferative Diabetic Retinopathy and Proliferative Vitreoretinopathy", Current Eye Research, pp. 1045-1053, Oxford University Press (1995).

S. Mandel, et al., "cDNA Microarray to Study Gene Expression of Dopaminergic Neurodegeneration and Neuroprotection in MPTP and 6-Hydroxydopaine Models: Implications for Idiopathic Parkinson's Disease", pp. 117-124, vol. 60, J. Neural, Springer-Verlag. (2000).

M. Bedard, et al., Release of Interleukin-8, Interleukin-6, and Colony-Stimulating Factors by Upper Airway Epithelial Cells: Implications for Cystic Fibrosis, pp. 455-462, vol. 9, American Journal of Respiratory Cell and Molecular Biology (1993).

P. L. Zeitlin, et al., "A Cystic Fibrosis Bronchial Epithelial Cell Line: Immortalization by Adeno-12-SV40 Infection", pp. 313-319, vol. 4, American Journal of Respiratory Cell and Molecular Biology (1991).

M.J. Welsh, et al., "Cystic Fibrosis", pp. 5121-5183, Chapter 201 Part 21 Membrane Transport Disorders (2001).

P. G. Gibson, et al., "Heterogeneity of Airway Inflammation in Persistent Asthma: Evidence of Neutrophilic Inflammation and Increased Sputum Interleukin-8", pp. 1329-1336, vol. 119(5), Ovid: Gibson, Chest, The Cardiopulmonary and Critical Care Journal (2001).

N. Kostulas, et al., "Increased IL-1[beta], IL-8, and IL-17 mRNA Expression in Blood Mononuclear Cells Observed in a Prospective Ischemic Stroke Study", American Heart Association, Inc., pp. 2174-2179, vol. 30(10), Lippincott, Williams & Wilkins.(1999).

Matsumoto, et al., "Pivotal role of interleukin-8 in the acute respiratory distress syndrome and cerebral reperfusion injury", Journal of Leukyocyte Biology, vol. 62, (1997).

M.Ol. Osman, et al., "A Monoclonal Anti-Interleukin-8 Antibody (WS-4) Inhibits Cytokine Response and Acute Lung Injury in Experimental Severe Acute Necrotizing Pancreatitis in Rabbits", pp. 232-239, vol. 43(2), Gut—An International Journal of Gastroenterology and Hematology. (1998).

Bhatia, M, et al., "Inflammatory Mediators As Therapeutic Targets in Acute Pancreatitis", MEDLINE, Pub. Med. Article Abstract web site page, Infotrieve, Inc. England (2001).

AMPHIPHILIC PYRIDINIUM COMPOUNDS, METHOD OF MAKING AND USE THEREOF

This application claims priority from U.S. Provisional Application Ser. No. 60/482,764 filed Jun. 27, 2003. The entirety of that provisional application is incorporated herein by reference.

This invention was made with United States Government support. The Government may have certain rights in the invention.

FIELD OF THE INVENTION

The present invention relates to the amphiphilic pyridinium compounds, method of making and method of using such compounds for the treatment of the interleukin-8 related diseases, such as cystic fibrosis.

BACKGROUND OF THE INVENTION

Interleukin-8 (IL-8) is a cytokine that activates and attracts neutrophils and attracts T-lymphocytes. IL-8 is released by several cell types including monocytes, macrophages, T-lymphocytes, fibroblasts, endothelial cells, and keratinocytes by an inflammatory stimulus. IL-8 is a member of the beta-thromboglobulin superfamily and structurally related to platelet factor 4.

IL-8 is a non-glycosylated protein of 8 kDa (72 amino acids) and is produced by processing of a precursor protein of 99 amino acids. The IL-8 protein contains four cysteine residues participating in disulfide bridges. The human IL-8 gene (SCYB8) has a length of 5.1 kb, contains four exons and maps to human chromosome 4q12-q21. The mRNA consists of a 101 base 5' untranslated region, an open reading frame of 297 bases, and a long 3' untranslated region of 1.2 kb. The 5' flanking region of the IL-8 gene contains a number of cis-acting elements that are potential binding sites for nuclear factors. Some of the cis-acting elements are responsive to intrinsic regulators such as NFκB and AP-1, while others are pathogen-specific. The identities of the cis-acting elements are summarized as follows: (i)RSVRE, (binding site –162 to –132) is the newly discovered Respiratory Syncytial Virus Responsive Element, which is responsible for the intense IL-8-dependent pulmonary inflammation in RSV infection [Casola et al, *J. Immunol.*, 164:5944-5951, (2000)]. (ii) IFNRF1,the Interferon Regulating Factor 1, binds to and further activates the RSVRE. [Casola et al, supra]. (iii) AP-1, (binding site: –126 to –120), is activated by the heterodimer of JunD/cFos, and is superactivated in cytomegalic virus (CMV) infection by the (iv) CMVRE1 (CMV Responsive Element). (v) NF-IL6 (binding site: –94 to –81) is activator of IL-8 transcription and is a possible overlapping site of interaction with C/EBPa (CCAAT box enhancer binding protein a). (vi) NFκB (binding site: –80 to –70) is activated by the family of NF B/Re1 transcription factors, and super-activated by CMV1E1. (vii) C/EBPa (binding site: –91 to –81) partially overlaps the NFκB site, and either activates or inhibits IL-8 transcription depending on the context [Victor et al, J. Trauma, 39:635-640, (1996); Stein et al., *Mol. Cell. Biol.*, 13:7191-7198, (1993)]. (viii) GC (glucocorticoid receptor) binds to NFκB and inhibits transcription [Baldwin, *Annu. Rev. Immunol.*, 14:649-681, (1996)]. (ix) OCT-1 is a homeodomain factor that suppresses IL-8 transcription by acting on NF-IL6 [Wu et al, J. Biol. Chem., 272:2396-2403, (1997)]. (x) NF-AT (Nuclear Factor of Activated T cells) binds at or near the NFκB site and activates transcription [Roebuck, J. Interferon Cytokine Res., 19:429-438, (1999)]. (xi) TAX, coded by HTLV-1, binds to NFκB and promotes transcription [Suzuki et al, *Oncogene*, 9:3099-3105, (1994)]. (xii) NRF (binding site: partial overlap with NFκB) is the NFκB Repressing Factor which is principally responsible for basal silencing, but is also required for full IL-8 mRNA production [Nourbakhsh et al, *J. Biol. Chem.*, 44:4501-4508, (2000)]. (xiii) TATA box (binding site: –20 to –13) binds TF-III and the TBP, and is absolutely required for IL-8 transcription.

IL-8 differs from all other cytokines in its ability to specifically activate neutrophil granulocytes. In neutrophils, IL-8 causes a transient increase in cytosolic calcium levels and the release of enzymes from granules. IL-8 also enhances the metabolism of reactive oxygen species and increases chemotaxis and the enhanced expression of adhesion molecules. A pre-activation by IL3 is required to render basophils and neutrophils susceptible to further activation by IL-8, and IL-8 alone does not release histamines. IL-8 actually inhibits histamine release from human basophils induced by histamine-releasing factors, CTAP-3 (connective tissue activating protein-3) and IL3.

L8 is chemotactic for all known types of migratory immune cells and inhibits the adhesion of leukocytes to activated endothelial cells, and therefore, possesses anti-inflammatory activities. IL-8 is a mitogen for epidermal cells and strongly binds to erythrocytes in vivo. This absorption may be of physiological importance in the regulation of inflammatory reactions since IL-8 bound to erythrocytes no longer activates neutrophils. Macrophage derived IL-8 supports angiogenesis and may play a role in angiogenes dependent disorders such as rheumatoid arthritis, tumor growth, and wound healing.

IL-8 expression and regulation have been associated a variety of disease conditions such as inflammatory bowel disease, atherosclerosis, and lung disorders. IL-8 has been specifically associated with cystic fibrosis (CF) because it is profoundly elevated in bronchoalveolar lavage fluids, sputum, and serum from CF patients [Dean et al, *Pediatr. Res.*, 34:159-161, (1993) and Armstrong et al, *Am J. Resnir. Crit. Care Med.*, 156:1197-1204, (1997)].

CF is the most common autosomal recessive lethal disease in the United States [Welsh et al, Cystic fibrosis in: The metabolic and molecular bases of inherited diseases (Scriver, C. L., Beaudet, A. L., Sly, W. S., and Valle, D. eds.) Seventh Ed. pp. 3799-3876, McGraw-Hill, New York. (1995)]. Approximately 5% of the population carries one mutant cystic fibrosis transmembrane conductance regulator (CFTR) gene [Rommens et al, *Science*, 245:1:1059-1065, (1989); Riordan et al, *Science*, 245:1:1066-1073, (1989); and Kerem et al, *Science*, 245:1:1073-1080, (1989)], and the disease occurs at a frequency of 1 in 2500 live births. Statistically, death occurs in the majority of patients by age 28. Respiratory difficulties and ensuing complications of inflammation and lung infection are directly responsible for the eventual death of over 90% of CF patents.

The CF lung has been described as microscopically normal at birth, with subtle abnormalities in mucus secretion appearing very early [Pilewski et al., *Physiol. Rev.*, 79:5215-5255, (1999)]. Bacterial infection and objective evidence of inflammation occur at later times, with a clear temporal evolution of different principal bacterial pathogens. For example, *Staphylococcus aureaus* and *Hemophilus influenzae* take up residence in the CF airway early, the mean age of positive culture being 12.4 months [Abman et al, *J. Pediatrics* 119:211-217, (1991)]. By comparison, *Pseudomonas aeruginosa* infection follows at a substantially later time, the mean age of first positive culture being 20.8 months. Persistent colonization by *P. aeruginosa* characterizes the older CF patient, and profound, persistent cellular evidence of inflammation accompanies persistent infection as the patient approaches the terminal phases of the disease.

As the CF patient ages, the CF lung becomes characterized by elevated levels of white cells. These include polymorphonuclear leukocytes, macrophages, monocytes, lymphocytes and eosinophils. It is suggested that these cells are attracted from the circulation into the airway by the high levels of IL-8 and other pro-inflammatory factors such as IL1β, IL6, leukotriene B$_4$, RANTES, and TNFα. These factors mark the character of the CF lumenal milieu [Bonfield et al, *Am. J. Respir. Mol. Biol.*, 13:257-261, (1995); and Bonfield et al, *Am. J. Respir. Mol. Biol.*, 125:2111-2118, (1995)], and among these factors, IL-8 ranks as the most prevalent and potent.

SUMMARY OF THE INVENTION

The present invention is directed to an pyridinium compound having a structure of formula I

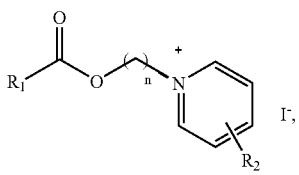

or formula II

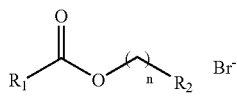

wherein in said Formula I, R$_1$ is selected from the group consisting of:

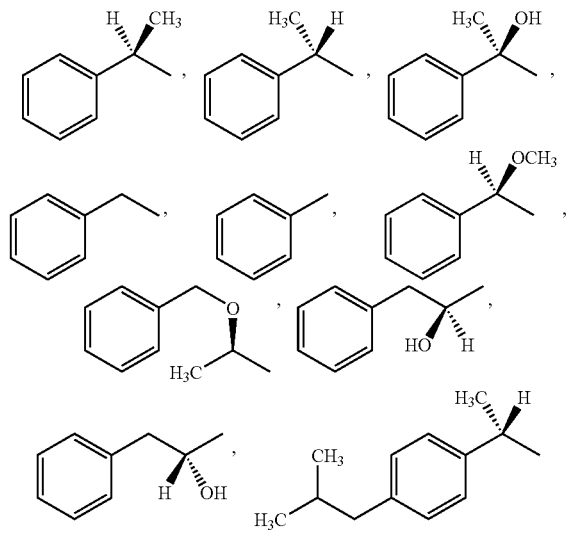

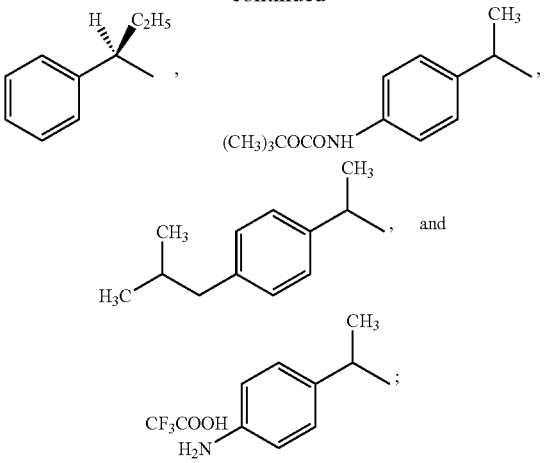

R$_2$ is selected from the group consisting of H and 3—CONH$_2$, and n is an integer between 8 and 10;

wherein in said Formula II, R$_1$ is

R$_2$ is selected from the group consisting of: p—(CH$_2$)$_2$CH$_3$, p—(CH$_2$)$_2$OH,

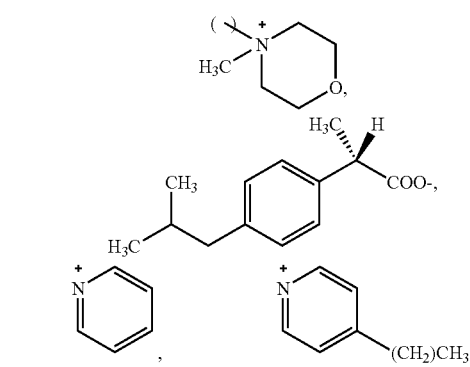

and n is an integer of 8.

The present invention also provides methods of making such amphiphilic compounds.

The present invention provides methods of using such amphiphilic compounds for suppressing IL-8 secretion and production, and the present invention further provides methods of using these compounds as therapeutics for the treatment of IL-8 related diseases, such as cystic fibrosis.

DETAILED DESCRIPTION OF THE INVENTION

Figure 1:
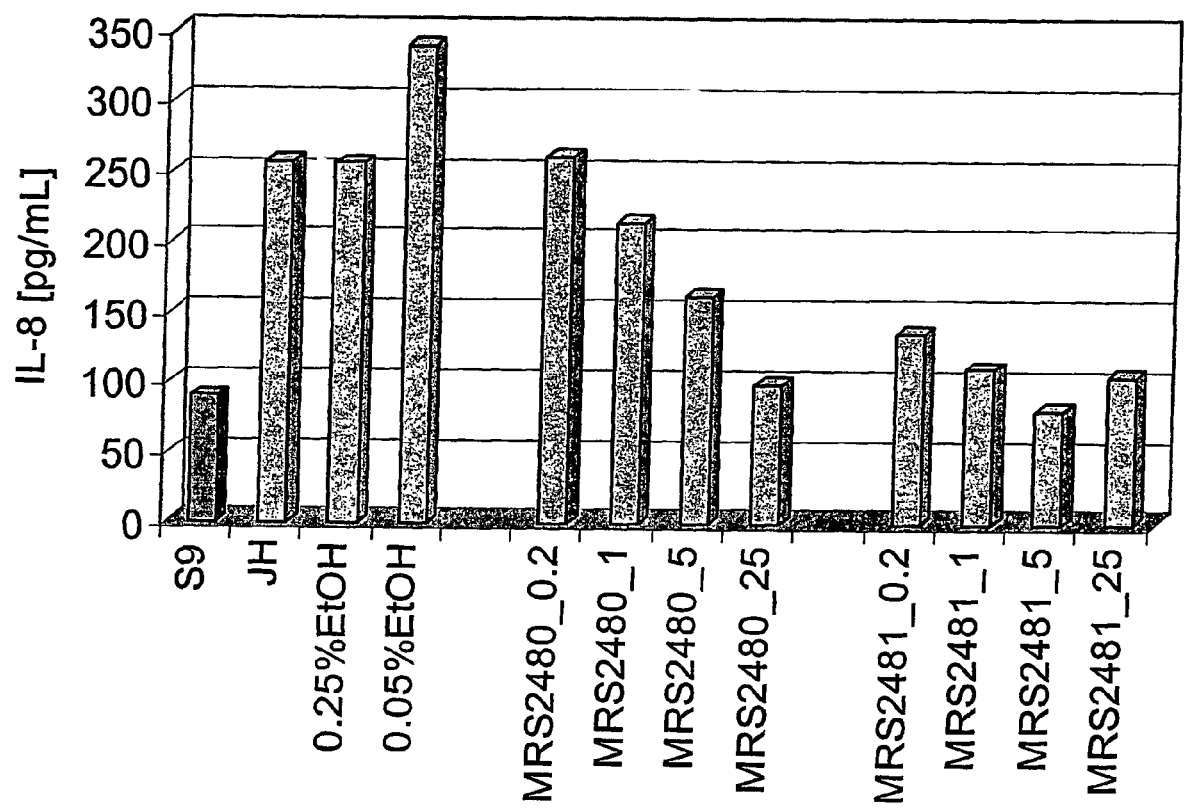
FIG. 1 illustrates suppression of IL8 secretion by different concentrations of amphiphilic compounds of the MRS2480 and MRS2481.

The following detailed description is presented to enable any person skilled in the art to make and use the invention. For purposes of explanation, specific nomenclature is set forth to provide a thorough understanding of the present invention. However, it will be apparent to one skilled in the art that these specific details are not required to practice the invention. Descriptions of specific applications are provided only as representative examples. Various modifications to the preferred embodiments will be readily apparent to one skilled in the art, and the general principles defined herein maybe applied to other embodiments and applications without departing from the scope of the invention. The present invention is not intended to be limited to the embodiments shown, but is to be accorded the widest possible scope consistent with the principles and features disclosed herein.

One aspect of the present invention relates to amphiphilic pyridinium compounds capable of inhibiting IL-8 secretion in mammalian cells. Table 1. Structures of the Amphiphilic Pyridinium Compounds of the Present Invention.

| Compound | R1 | n | R2 |
|---|---|---|---|
| Formula I | | | |
| 1<br>MRS 2572 | (S)-1-phenylethyl (H, CH$_3$, phenyl) | 4 | H |
| 2<br>MRS 2573 | (S)-1-phenylethyl | 6 | H |
| 3<br>MRS 2481 | (S)-1-phenylethyl | 8 | H |
| 4<br>MRS 2574 | (S)-1-phenylethyl | 10 | H |
| 5<br>MRS 2485 | (R)-1-phenylethyl (H$_3$C, H, phenyl) | 8 | H |

-continued
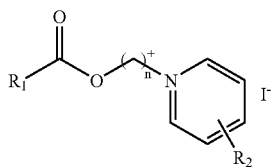
(Formula I)
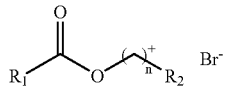
(Formula II)
| Compound | R1 | n | R2 |
|---|---|---|---|
| 6 MRS 2515 | H₃C, OH on C(CH₃)(Ph) | 8 | H |
| 7 MRS 2480 | PhCH₂– | 8 | H |
| 8 MRS 2591 | Ph-CH(C₂H₅)(CH₃) | 8 | H |
| 9 MRS 2506 | Ph-CH(OCH₃)(CH₃) | 8 | H |
| 10 MRS 2507 | PhCH₂-O-CH(CH₃)– | 8 | H |
| 11 MRS 2513 | Ph– | 8 | H |
| 12 MRS 2514 | PhCH₂-CH(OH)(CH₃) | 8 | H |
| 13 MRS 2516 | PhCH₂-CH(OH)(CH₃) (enantiomer) | 8 | H |
| 14 MRS 2590 | 4-(isobutyl)phenyl-CH(CH₃)– | 8 | H |

-continued

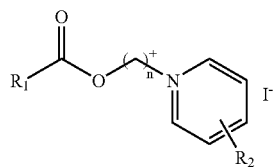

(Formula I)

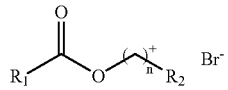

(Formula II)

| Compound | R1 | n | R2 |
|---|---|---|---|
| 15 MRS 2390 | (S)-1-(4-isobutylphenyl)ethyl | 8 | H |
| 16 MRS 2517 | 4-(1-methylethyl)-N-(pivaloylamino)phenyl [(CH₃)₃COCONH-C₆H₄-CH(CH₃)₂] | 8 | H |
| 17 MRS 2518 | 4-(1-methylethyl)-anilinium trifluoroacetate [CF₃COOH·H₂N-C₆H₄-CH(CH₃)₂] | 8 | H |
| 18 MRS 2589 | 4-isobutyl-α-methylbenzyl | 8 | 3-CONH$_2$ |
| 19 MRS 2421 | (S)-1-(4-isobutylphenyl)ethyl | 8 | p-CH$_2$CH$_2$CH$_3$ |
| Formula II | | | |
| 20 MRS 2423 | (S)-1-(4-isobutylphenyl)ethyl | 8 | p-(CH$_2$)$_2$—OH |
| 21 MRS 2422 | (S)-1-(4-isobutylphenyl)ethyl | 8 | 4-methylmorpholinium |

-continued (Formula I)

(Formula II)

| Compound | R1 | n | R2 |
|---|---|---|---|
| 22 MRS 2391 | [4-isobutylphenyl, (S)-α-methyl] | 8 | [4-isobutylphenyl, (S)-α-methyl, COO–] |
| 23 | [4-isobutylphenyl, α-methyl] | 8 | pyridinium |
| 24 | [4-isobutylphenyl, α-methyl] | 8 | 4-ethylpyridinium (CH$_2$)CH$_3$ |

Another aspect of the present invention relates to the synthesis of the amphiphilic pyridinium compounds of Table I. Briefly, these compounds are synthesized by the following schemes:

In scheme 1, a) is mixing $C_6H_5N(CH_3)_3OH$ and TBAI at room temperature (R.T.) for 2 days, b) is mixing NaI in acetone, and c) is pyridine derivative in acetone at 50° for 3 days.

Scheme 1:

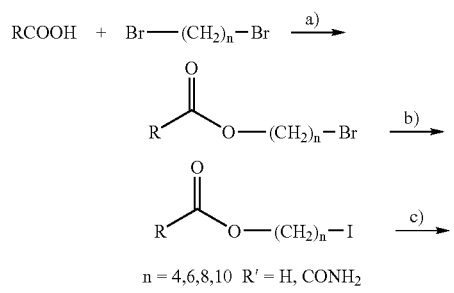

n = 4,6,8,10  R' = H, CONH$_2$

Compound 1–15 and 18

Scheme 2:

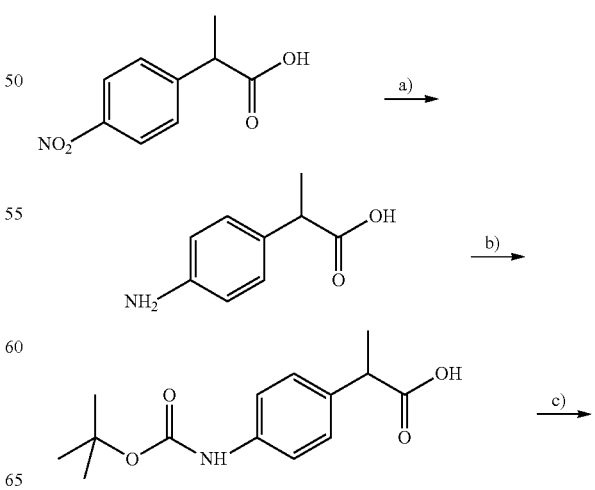

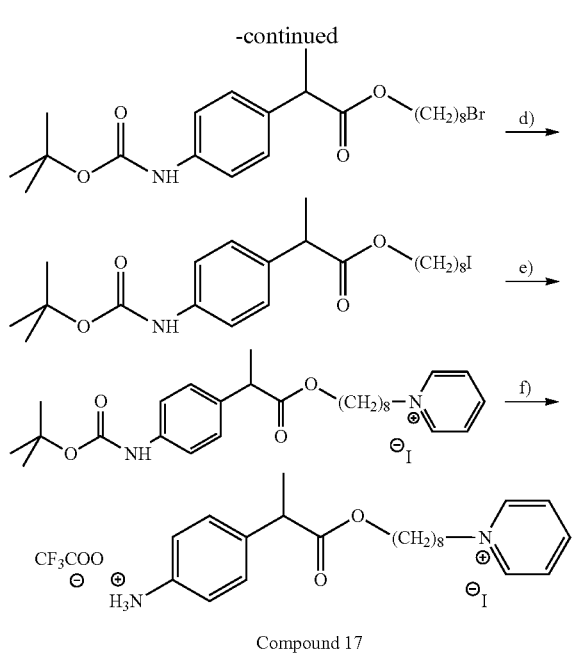

Compound 17

In Scheme 2, a) is mixing Sn, AcOH, and HCl at 100° C. for 1.5 hour, b) is mixing (tButyl)$_2$carbonate in MeOH at 45° C. for 1 hour, c) is mixing C$_6$H$_5$N(CH$_3$)$_3$OH and TBAI at R.T. for 2 days, d) is mixing NaI in acetone, e) is pyridine derivative in acetone at 50° for 3 days and f) is TFA.

In Scheme 3, a) is mixing Dibromooctane, C$_6$H$_5$N(CH$_3$)$_3$OH and TBAI at R.T. for 3 days, b) is mixing 4-Methylmorfoline, TBAI in acetone at 50° for 2 days, c) is mixing 4-propyl-py and TBAI in acetone at 50° for 3 days, and d) is mixing 4—OH-ethyl-py TBAI in acetone at 50° for 3 days.

Yet another aspect of the present invention relates to the treatment of the IL-8 related diseases or conditions with the amphiphilic pyridinium compounds of Table I. Examples of IL-8 related diseases and conditions include, but are not limited to, lung disorders and conditions such as cystic fibrosis, cardiopulmonary bypass operations, cardiopulmonary arrest, inflammatory bowel disease, atherosclerosis, thermal injuries, acid injury, smoke inhalation, reexpansion pulmonary edema, traumatic brain injury, stroke, diabetes, transplant graft rejection, Alzheimer's disease, Parkinson's disease, viral infections such as HIV, cancer, cyclooxygenase inhibitors resistant fevers, rheumatoid arthritis and related inflammatory disorders.

In one embodiment, at least one of the amphiphilic pyridinium compounds of Table I is administered to a mammal for the treatment of CF. In a preferred embodiment, the amphiphilic pyridinium compounds comprise at least one of Compounds 3 (MRS2481), 4 (MRS 2574), 7 (MRS 2480), 8 (MRS 2591), 15 (MRS2390),16 (MRS 2517),18 (MRS 2589) and 19 (MRS2421). In a more preferred embodiment, the amphiphilic pyridinium compound(s) comprise Compounds 3, 4, 8, 15, 16, 18 and 19. In a most preferred embodiment, the amphiphilic pyridinium compounds comprise Compounds 3. IL-8 is profoundly elevated in bronchoalveolar lavage fluids, sputum, and serum from CF patients [Dean et al, *Pediatr. Res.*, 34:159-161, (1993), Richman-Eisenstat et al, *Am. J. Physiol.*, Scheme 3:

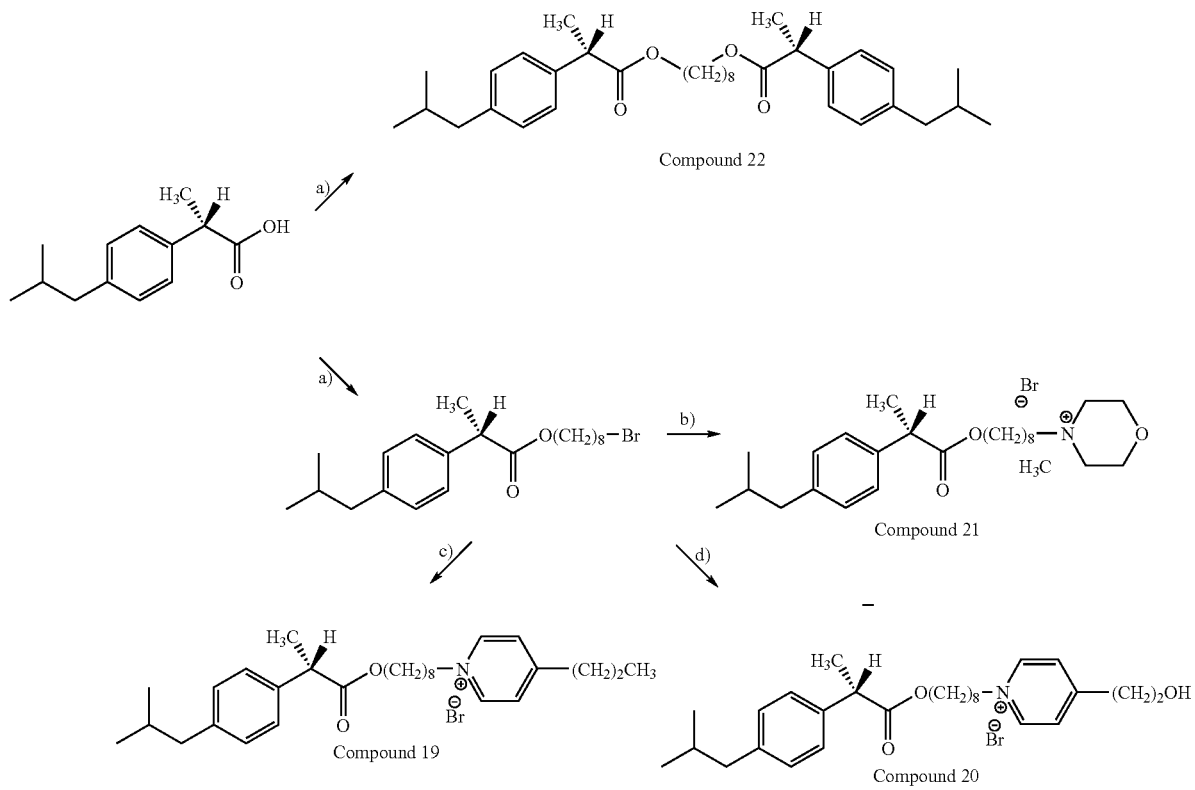

264:L413-418, (1993); and Armstrong et al, *Am J. Resnir. Crit. Care Med.,* 156:1197-1204, (1997)]. Importantly, hypersecretion of IL-8 occurs prior to objective evidence of infection by viruses, fungi or common CF pathogenic bacteria [Khan et al, *Am J Respir Crit Care Med.,* 151(4):1075-82. (1995)]. The generality of a pro-inflammatory state for CF epithelia is further proven by the fact that fecal IL-8 levels in CF children are approximately 1000-fold elevated over non-CF controls [Briars et al, *J. Biol. Chem.,* 273:3551-3556, (1995)]. Fecal IL-8 levels are correlated with lung function (FEV1, forced expiratory volume in one second), and only to some extent with established *Pseudomonas* infection. Biopsies from CF patients undergoing lung transplant have demonstrated consistent up-regulation of IL-8 expression in sub-mucosal gland cells [Tabary et al, *Am J. Path.,* 153:921-930, (1998)]. Based on these clinical criteria, high IL-8 levels would be intrinsic to the CF lung.

Airway epithelial cells isolated from CF patients consistently secrete more IL-8 than do cells cultured from patients without CF [Bedard et al, *Am. J. Resp. Cell Mol. Biol.,* 9:455-462, (1993); Ruef et al, *Eur. Resp. J.,* 6:1429-1436, (1993); DiMango et al, *J. Clin. Invest.,* 96:2204-2210, (1998)]. It has been proposed that high IL-8 secretion plays an important role in the CF lung epithelial cells, and is likely to be caused by mutant CFTR. Accordingly, the pyridinium compounds of the present invention capable of reducing IL-8 secretion are useful as therapeutics in the treatment of CF.

In another embodiment, the amphiphilic pyridinium compound(s) of Table I is administered to a mammal during and after operation cardiopulmonary bypass operations to reduce IL-8 associated adverse reactions. Cardiopulmonary bypass operations are associated with a transient rise in circulating IL-8 and other cytokines [Nandate et al, *Anesth. Analg.,* 89:823-828, (1999)]. Brain dysfunction following the operation occurs in some patients, and the mechanism may involve activation of inflammatory processes in the brain. It was shown that during and following the bypass operation, IL-8 levels are consistently higher in the jugular bulb, containing blood coming from the brain to the heart, than in the paired arterial samples [Nandate et al, supra]. Specific and significant IL-8 production could be found to be produced in the cerebrovascular bed during and following the operation. It was reported that at least one intervention, hypothermia, suppresses the changes. For example, the apolipoprotein E4 allele is associated with increased propensity to atherosclerosis, higher levels of lipoprotein, and early Alzheimer's Disease. Patients carrying the apolipoprotein E4 allele have higher baseline levels of IL-8 and TNFα than patients lacking this alleles [Drabe et al., *Eur. J. Cardiothorac. Surg.,* 20:609-613, (2001)]. Following cardiopulmonary bypass, the apolipoprotein E4 patients, comprising 27% of the patient cohort, also have increased release of both IL-8 and TNFα, compared to patients lacking this allele. It is therefore suggested that patients with the E4 genotype should have additional perioperative therapy for the aberrantly increased systemic inflammatory response. Thus, the pyridinium compounds of the present invention that interfere with IL-8 production are useful in ameliorating morbidity and mortality associated with cardiopulmonary bypass operations.

In another embodiment, the amphiphilic pyridinium compound(s) of Table I is administered to a mammal for the treatment of cardiopulmonary arrest. Patients arriving in the hospital emergency room after suffering cardiopulmonary arrest (CPA) have increased levels of serum IL-8 and TNFα. These levels peak within 12 hours post-admission, or within 6 hours after return of spontaneous circulation (ROSC) [Ito et al, *Resuscitation,* 51:47-53, (2001)]. Serum of IL-8 levels in those patients with significantly higher levels of IL-8 tend to die or become brain dead within one week of return of spontaneous circulation (Ito et al., supra). Excessive administration of epinephrine is also associated with significantly elevated levels of IL-8 following return of spontaneous circulation. Thus, the pyridinium compounds of the present invention that interfere with IL-8 production are useful in ameliorating morbidity and mortality associated with cardiopulmonary arrest.

In another embodiment, the amphiphilic pyridinium compound(s) of Table I is administered to a mammal for the treatment of inflammatory bowel diseases. IL-8 and other chemokines have been implicated in the pathogenesis of inflammatory bowel disease [Imada et al, *Scand. J. Gastroent.,* 36:854-864, (2001)]. The levels of IL-8 are especially elevated in acute organ cultures of patients with active ulcerative colitis. The increased expression of IL-8 message can be detected in macrophages, pericrypt myofibroblasts and epithelium (Imada et al., supra). Dietary fat has been proposed to exacerbate intestinal inflammation, and studies with mono layers of colon epithelial cells indicate that medium-chain fatty acids such as oleic acid cause a five-fold elevation of IL-8 secretion [Tanaka et al, *J. Gastroent. Hepatol.,* 16:748-754, (2001)]. The process follows the anatomy of digestion, since the fatty acid is added on the apical (lumenal) side, while IL-8 secretion occurs in the baso-lateral (serosal) direction. Therefore, the pyridinium compounds of the present invention that interfere with IL-8 production are useful as therapeutics in the treatment of inflammatory bowel diseases.

In another embodiment, the amphiphilic pyridinium compound(s) of Table I is administered to a mammal for the treatment of atherosclerosis. Inflammation processes are associated with the pathogenesis of atherosclerosis, and high levels of IL-8 are found in atheromatous plaques [Wang et al, *J. Biol. Chem.,* 271:8837-8842, (1996)]. The processes regulating IL-8 synthesis can be studied in vitro in cultures of human aortic endothelial cells. IL-8 is synthesized in these cells via multiple convergent pathways [Tanaka et al, *J. Gastroent. Hepatol.,* 16:748-754, (2001)]. For example, prevastatin (an inhibitor of 1,3-hydroxy-3-methylglutaryl co-enzyme A reductase) not only lower cholesterol, but also suppresses thrombin-induced L-8 production in these cells cultured in high glucose medium. The effect is not on the baseline of IL-8 levels, but on stimulated levels induced by thrombin. The mechanism involves inhibition of the thrombin-induced transition of ras from the cytosol to the plasma membrane. The consequence is suppression of activation of the ras-MAP (p44/42) kinase pathway, but not the kinase itself. Therefore, the pyridinium compounds of the present invention that specifically target IL-8 production are useful in treating inflammatory aspects of atherosclerosis.

In another embodiment, the amphiphilic pyridinium compound(s) of Table I is administered to a mammal for the treatment of lung disorders and conditions, other than cystic fibrosis. While IL-8 levels in CF lungs are tonically elevated over controls by 1000 fold or more, much more modest levels of IL-8 elevation, in the range of 2-10 fold, have been observed in some other pulmonary diseases and disorders. Modest but significant elevations of IL-8 have been reported in noneosinophilic asthma [Gibson et al, *Chest.,* 119:1329-1336, (2001)]. IL-8 levels in asthmatic children are detectable, and are correlated with symptoms [Marguet et al, *Pediatr. Allergv Immunol.,* 12:27-33, (2001)]. Somewhat elevated IL-8 levels have been found in asymptomatic nonspecific airway hyperresponsiveness (BHR) [Betz et al, *Lung,* 179: 119-133, (2001)]. Patients with chronic obstructive pulmonary disease (COPD), sometimes used as a control for cystic fibrosis, also have high levels of IL-8 (Betz et al, supra). It has been suggested that BHR and COPD are temporally related because asymptomatic BHR can progress to COPD. Generally, multi-trauma patients often develop nosocomial pneumonia (NP), and a higher level of IL-8 in bronchoalveolar lavage fluids of the incoming patient is predictive of the development of NP [Muehlstedt et al, *Surgery*, 130:602-609, (2001)]. For these reasons, the pyridinium compounds of the present invention that specifically target IL-8 production are useful in treating and/or preventing asthma, BHR, COPD, and NP.

In another embodiment, the amphiphilic pyridinium compound(s) of Table I is administered to a mammal for the treatment of thermal injuries (e.g. burns). Burns are closely associated with increases in cytokines such as TNF, IL-6 and IL-8 in the systemic circulation, normal and thermally injured skin and lung [Rodriguez et al, *J. Trauma.*, 34:684-694, (1993); and Vindenes et al, *J. Trauma.*, 39:635-640, (1995)]. The lung cytokine response to acute thermal injury may be responsible for initiating local organ failure. The highest levels of IL-8 are associated with septic patients who died [Yeh et al, *Burns*, 23:555-559, (1997), and high IL-8 levels are also associated with delayed healing of thermal wounds, by suppression of fibroblast replication and, inhibition of myosin ATPase [Iocono et al, *Wound Repair Regeneration*, 8:216-225, (2000)]. Therefore, the pyridinium compounds of the present invention that interfere with IL-8 production are useful as therapeutics in the treatment of thermal injuries.

In another embodiment, the amphiphilic pyridinium compound(s) of Table I is administered to a mammal for the treatment of acute pancreatitis. Acute pancreatitis in humans is often associated with multi-organ dysfunction syndrome (MODS), principally affecting the lung [Bhatia et al. *Curr. Opin. Invest. Drugs*, 2:496-501, (2001)]. Experimental acute pancreatitis models have been studied in rabbits, in which IL-8 is elevated in serum and lung, and acute lung injury observed [Osman et al, *Gut*, 43:232-239, (1998); and Osman et al, *Eur. J. Gastroenterol. Hepatol.*, 11:137-149, (1999)]. Infusion of an antibody against IL-8 during the acute pancreatitis prevents lung damage, as evidenced by reduced neutrophil infiltration in the lung, while pancreatic necrosis and systemic release of pancreatic enzymes is unaffected (Osman et al, supra, 1998). Therefore, the pyridinium compounds of the present invention which suppress IL-8 production during acute pancreatitis are useful in suppressing MODS.

In another embodiment, the amphiphilic pyridinium compound(s) of Table I is administered to a mammal for the treatment of smoke inhalation. Smoke inhalation as found in victims of fires or injured firemen, causes lung endothelial injury and formation of pulmonary edema. Laffon et al (1999) have developed a rabbit model in which cooled smoke causes significant increasing in alveolar epithelial permeability and a significant reduction in bidirectional transport of protein across the pulmonary epithelium [Laffon et al., *Am. J. Respir. Crit. Care Med.*, 160:1443-1449, (1999)]. Laffon et al (1999) show that administration of an anti-IL-8 antibody restores alveolar epithelial permeability to normal levels and significantly increases bidirectional transport of protein. Thus increased IL-8 is an important mediator of lung injury following smoke inhalation, and the pyridinium compounds of the present invention capable of suppressing IL-8 production are useful as therapeutics for smoke inhalation lung injury.

In another embodiment, the amphiphilic pyridinium compound(s) of Table I is administered to a mammal for the treatment of acid injury. Acid injury to the lung is associated with an increase in alveolar epithelial permeability to protein and a reduction in net alveolar fluid clearance [Modelska et al, *Am. J. Respir. Crit. Care Med.*, 160:1441-1442, (1999)]. Pretreatment with an anti-IL-8 antibody significantly reduces the acid mediated increase in bi-directional transport of protein across the alveolar epithelium and restores alveolar fluid clearance to normal (Modelska et al, supra). Thus, the pyridinium compounds of the present invention capable of suppressing IL-8 production should be the useful therapeutics for the lung acid injury.

In another embodiment, the amphiphilic pyridinium compound(s) of Table I is administered to a mammal for the treatment of reexpansion pulmonary edema (REPE). REPE often follows reexpansion of a collapsed lung due to a mechanism of increased microvascular permeability and inflammatory cell accumulation [Nakamura et al, *Am. J. Respir. Crit. Care Med.*, 161:1030-1036, (2000)]. Local overproduction of IL-8 is responsible for the process. Pretreatment with anti-IL-8 antibody significantly reduces the neutrophil count in broncho alveolar lavage (BAL) fluid and suppresses REPE. Thus, the pyridinium compounds of the present invention capable of suppressing IL-8 production are useful as therapeutics for reexpansion pulmonary edema in the lung.

In another embodiment, the amphiphilic pyridinium compound(s) of Table I is administered to a mammal for the treatment of traumatic brain injury and stroke. Following traumatic brain injury, increases occurring in the levels of IL-8 and other proinflammatory cytokines [Ott et al, *J. Neurotrauma*, 11:447-472, (1994)]. Children with severe head injuries, there is a significant association between survival after traumatic brain injury and levels of IL-8 in the cerebrospinal fluid (CSF) [Whalen et al, *Crit. Care. Med.*, 28:1221-1234, (2000); see also Sherwood et al., *Crit. Care. Med.*, 28:1221-1223 (2000)]. IL-8 and related agents play a central role in the cellular cascade of injury, both centrally and peripherally by inducing fever, neutrophilia, muscle breakdown, altered amino acid metabolism, depression of serum zinc levels, production of hepatic acute phase reactants, increased endothelial permeability and expression of endothelial adhesion, molecules. [Ott et al, *J. Neurotrauma*, 11:447-472, (1994)]. Further, specific failures of gut, liver and lung have been identified due to IL-8 and other brain-derived cytokines such as IL-1, IL-6, and TNFα. [Ott et al., supra]. In addition, the brain origin of circulating IL-8, IL-1 and IL-6 have been validated, in which following brain trauma, these interleukins are higher in cerebrospinal fluid (CSF) than plasma [Kossmann et al., *J. Cerebr. Blood. Flow Metab.*, 17:280-289, (1997); Maier et al., *Shock*, 15:421-426, (2001)]. Maximal values in IL-8 in CSF are also associated with destruction of the blood brain barrier (Kossmann et al, supra; Maier et al, supra). While there appears to be a role for IL-8 in stimulating repair in the brain by the NGF pathway (Kossmann et al, supra), the massively elevated IL-8 levels seen in traumatic brain injury appear to exert a strong, contrary pathophysiological connection to adverse consequences of traumatic brain injury. These data suggest that the pyridinium compounds of the present invention capable of suppressing IL-8 production should be the useful in reducing morbidity and mortality following traumatic brain injury, thereby permitting the occurrence of any positive reparative actions of low levels of IL-8.

In another embodiment, the amphiphilic pyridinium compound(s) of Table I is administered to a mammal for the treatment of stroke. Stroke, a localized ischemic trauma to the brain, significantly increases levels of IL-8 and other related factors in the cerebrospinal fluid (CSF). IL-8 levels increase immediately following stroke, and peak on day 2 [Tarkowski et al, *Clin. Exp. Immunol.*, 110:492-499, (1997]. Higher levels of IL-8 in the CSF are observed following white matter strokes than grey matter strokes. Following stroke, IL-8 mRNA levels in peripheral blood neutrophils remain increased for up to 30 days following stroke, while other cytokines return to normal [Kostulas et al., Stroke, 30:2174-2170, (1999)]. In animal models of stroke, intracysternal administration of blocking antibodies to IL-8 are found to prevent cerebral reperfision injury, and endotoxemia-induced acute respiratory distress syndrome-(ARDS)-like lung injury [Matsumoto et al, J. Leukoc. Bio., 62:581-587, (1997); Mukaida et al, Inflamm. Res., Suppl:S151-157, (1998)]. An intracysternal neutralizing IL-8 antibody has also been reported to reduce brain edema and infarct size in rabbit brain following experimental transient focal ischernia (Matsumoto et al, Lab Invest., 77:119-125, (1997)]. These data indicate that the pyridinium compounds of the present invention with the capacities to lower brain levels of IL-8 would be useful in the treatment and prevention of stroke.

In another embodiment, the amphiphilic pyridinium compound(s) of Table I is administered to a mammal for the treatment of diabetes. Diabetes is associated with an approximately 4-fold elevation in ambient serum IL-8 [Zozulinska et al, Diabetologia, 42:117-118, (1999)). The increment is valid for both type I and Type II diabetics, and is significantly correlated with levels of glycosylated hemoglobin ($HbA_{1c}$), and this study was performed in a set of diabetic patients with no evidence of acute or chronic infection, renal failure or ketoacidosis, and a set of age-matched controls. Supportive data have been reported by Yuuki et al on J. Diabetes Complications, 15:257-259, (2001). The IL-8 signal is a strong beacon for polymorphonuclear leukocytes, and the relationship is consistent with a pro-inflammatory phenotype for diabetes. Therefore, the pyridinium compounds of the present invention capable of suppressing IL-8 production should be useful for the treatment of complications of diabetes.

In addition, one of the major complications in diabetes is vascular damage in the retina due to high glucose. Proliferative diabetic retinopathy (PDR) is the most common cause of blindness in the U.S. and Western European population. Levels of IL-8 occur in the vitreous humor of diabetes patients with PDR are significantly higher. [Elner et al, Curr. Eye Res., 14:1045-1053, (1995) and Yuuki et al, J. Diabetes Complications, 15:257-259, (2001)]. In contrast, IL-8 levels in vitreous of non-diabetic patients with PDR, an analogous syndrome not associated with diabetes, are equivalent to control levels found in normal eyes. In addition, other conditions such as idiopathic macular holes, idiopathic macular puckers, vitreous hemorrhages, or uncomplicated retinal detachments have a phenotype of normal IL-8 levels in the vitreous.

Further, elevated IL-8 levels can be found only in active cases of PDR, but not inactive PDR cases. [Elner et al, Arch. Ophthal., 116:1597-1601, (1998)]. High glucose concentrations induce elevated IL-8 mRNA expression in cultured human aortic endothelial cells, but not smooth muscle cells [Temaru et al, Diabetologia, 40:610-613, (1997)]. These data suggest that diabetic macroangiopathy is caused by a glucose-dependent gradient of IL-8 between the smooth muscle and the arterial intima, and IL-8 participates in the pathogenesis of proliferative diabetic retinopathy. For these reasons, the pyridinium compounds of the present invention specifically suppressing IL-8 production are useful in treating diabetic complications such as diabetic retinopathy.

In another embodiment, the amphiphilic pyridinium compound(s) of Table I is administered to a mammal for the treatment of transplant graft rejection. Successful transplant surgery of kidneys, lungs and other organs depend upon high quality donor organs that tend not to be rejected by the recipient. Inflammation in the donor organ, as evidenced by high IL-8 levels, is associated with increased likelihood of graft rejection by the recipient [Zivna et al, Transpl. Proc., 31:2094, (1999)]. Increasing serum and urine IL-8 concentrations in recipients 24 hours after kidney transplant is predictive of future rejection episodes [Zivna et al, supra]. In the case of lung transplants, an increased level of IL-8 in the donor bronchoalveolar lavage (BAL) fluid is associated with severe early graft dysfunction and early recipient mortality [Fisher et al, Am. J. Respir. Crit. Care Med., 163:259-265, (2001)]. The severe trauma patients and the frequent source of lungs for transplant, often have increased levels of IL-8, as well as neutrophils that are attracted by IL-8. [Fisher et al, supra]. IL-8 levels are 10-fold lower in unrelated living renal transplants compared to cadaver kidneys [Stangl et al, Transplant. Proc. 33:1284-1285, (2001)]. Lower level of IL-8 is the reason for superior long term results from the living renal transplants. Thus, the pyridinium compounds of the present invention capable of suppressing IL-8 production are useful in reducing the incidence of rejection and recipient death.

In another embodiment, the amphiphilic pyridinium compound(s) of Table I is administered to a mammal for the treatment of Alzheimer's disease. Alzheimer's disease, affecting an ever increasing fraction of the aging population, is believed to be due to toxic effects of brain-derived amyloid beta peptide (AβP). The pathological. basis of AβP action on neurons is the increase in intracellular $Ca^{2+}$ via calcium channels formed by the AβP itself [Arispe et al, PNAS USA, 90:567-571, (1993); and Arispe et al, PNAS USA, 89:1539-1543, (1996)]. Among the consequences of this action are increasing in immune/inflammatory pathways associated with IL-8 in affected areas of the brain. Such affected areas include cortex and hippocampus. It was shown that AβP stimulates IL-8 secretion from human astrocytoma cells [Gitter et al., PNAS USA, 92:10738-10741, (1995)]. In addition, IL1b potentiates AβP action on IL-8 secretion by astrocytes by 10-fold, a process which is altogether blocked by calcium chelators such as EGTA. The immediate target of the secreted IL-8 may be IL-8 receptors, which are plentiful in the central nervous system. Further, it was reported that IL-8RB colocalizes with AβP-positive neuritis in Alzheimer's Disease brain, but not with paired helical filaments (PBF) or hyperphosphorylated tau (AT8) [Xia et al, Am. J. Path., 150:1267-1274, (1997)]. Thus, IL-8 plays an important role in normal brain for signaling between neurons and glia, and plays an important role in the brain of Alzheimer's disease to potentiate immune destruction of neurons. Accordingly, the pyridinium compounds of the present invention which interfere with IL-8 secretion in brain are useful as therapeutics for Alzheimer's disease.

In another embodiment, the amphiphilic pyridinium compound(s) of Table I is administered to a mammal for the treatment of Parkinson's disease. Parkinson's disease, caused by destruction of the substantia nigra pars compacta in the midbrain, joins Alzheimer's disease as one of the neurodegenerative disorders whose incidence is increasingly manifest in, the aging population. Polymorphisms of genes associated with the proinflammatory TNFα, pathway have been discovered and, interpreted as indicating a immunomodulatory effect on sporadic Parkinson's disease [Kruger et at, J. Neural. Transm., 107:553-562,(2000); Nishimura et al, Neurosci Lett., 311(1):1-4, (2001)]. TNFα may have a toxic effect on Parkinson's disease, implying action at the level of the substantia nigra in the brain. MPTP (N-methyl-1-4 phenyl.-1,2,3,6-tetrahydropyridine) is a neurotoxin which causes Parkinson's Disease-like syndrome in organisms as phylogenetically diverse as goldfish and man [Pollard et al, Anatomical Rec., 259:iii-ix, (1992); Goping et al, Brain Res., 678:35-52, (1995)]. Genes associated with inflammatory pathways have been shown to be induced in mouse brain by MPTP [Grunblatt et al, *J. Neurochem, Jul* 78(1):1-1.2, (2001); Mandel et al, *J. Neural Transm Suppl,* 2000:117-24, (2000)]. Since TNFα pathway terminates at the IL-8 promoter, the pyridinium compounds of the present invention capable of suppressing IL-8 production are useful as therapeutics for Parkinson's disease.

In another embodiment, the amphiphilic pyridinium compound(s) of Table I is administered to a mammal for the treatment of HIV and other viral infections. HIV-1 infection of macrophages result in elevation of IL-8 synthesis and secretion by the infected cells. Conversely, IL-8 stimulates HIV-1 replication in macrophages and T-lymphocytes [Lane et al, *J Virol.,* 75(17):8195-202, (2001)]. It was shown, consistently, that increased levels of IL-8 are presented in the lymphoid tissue of patients with AIDS. Furthermore, compounds which block IL-8 receptors also inhibit HIV-I replication in both T lymphocytes and macrophages. Thus, the pyridinium compounds of the present invention capable of interfering with IL-8 secretion are useful as therapeutics for HIV-I infection and AIDS.

Further, HIV-1 infected patients often develop neurological disorders and HIV-1 associated dementia following invasion of the brain by activated T cells and infected macrophages. HIV-1 Tat (72aa) peptide potently induces IL-8 and related cytokines in astrocytes [Kutsch et al, *J. Virol.,* 74:9214-9221, (2000)]. IL-8 message is observed within an hour and IL-8 protein is produced. Since IL-8 potentiates HIV-1 infection, the pyridinium compounds of the present invention capable of interfering with IL-8 secretion are useful in preventing or suppressing HIV-1 infections in the CNS leading to HIV-1-associated dementia.

Other viral agents have an impact, either directly or indirectly, on IL-8 production by target cells. In the case of adenovirus, the adenoviral gene product E1A primes alveolar epithelial cells to produce elevated levels of IL-8 when exposed to environmental particulate matter that is less than 10 microns in diameter (viz., PM(10)) or hydrogen peroxide ($H_2O_2$) [Gilmour et al, *Am. J. Physiol. Lung Ce. Mol. Physiol.,* 281:598-606, (2001)]. In the case of the human rhinovirus (HRV-14), a line of human bronchial epithelial cells the growth factors TNFα and EGF induced the cells to both synthesize increased levels of IL-8, and to support increased viral replication. [Subauste et al., *Int. Immunopharmacol.,* 1:1229-1234, (2001)]. In the case of respiratory syncytial virus (RSV), there is a well known responsive element for RSV on the IL-8 promoter (viz, the RSVRE) which supports a vastly increased level of IL-8 production upon RSV infection. Therefore, the pyridinium compounds of the present invention capable of interfering with IL-8 production are useful as therapeutics in treating some viral infections, or suppressing associated inflammatory symptoms.

In another embodiment, the amphiphilic pyridinium compound(s) of Table I is administered to a mammal for the treatment of cancer. Adenoviral gene therapy with antisense to IL-8 has been successful in reducing growth of human bladder tumor cells growing subcutaneously in the nude mouse [Inoue et al, *Oncol. Rep.,* 8:955-964, (2001)]. The injections of the adenoviral construct were directly into the body of the tumor, and only resulted in inhibition of growth rate relative to control capacity. The pyridinium compounds of the present invention capable of interfering with IL-8 production are useful in interfering with tumor growth, development or metastasises.

In another embodiment, the amphiphilic pyridinium compound(s) of Table I is administered to a mammal for the treatment of fever that is resistant to cyclooxygenase inhibitors. Certain fevers are known to be resistant to cyclooxygenase inhibitors, and a type of fever caused by intracerebrovascular injection of IL-8 falls into this category [Zampronio et al, *Am. J. Physiol.,* 266:R1670-1674, (1994)]. Therefore, the pyridinium compounds of the present invention capable of interfering with IL-8 secretion in brain cells are useful as antipyretics for fevers resistant to cyclooxygenase inhibitors.

In another embodiment, the amphiphilic pyridinium compound(s) of Table I is administered to a mammal for the treatment of psoriasis. Psoriasis is a disabling, proliferative skin disorder associated with systemic elevation of lymphocytes [Hoxtermann et al, *Dermatology,* 196:223-230, (1998)] and other evidences of aberrant cytokine production [Stoof et al, *Br. J. Dermatol,* 144:1114-1120, (2001)]. It was shown that the antipsoriatic drug dimethylfumarate (DMF), in the range of 5-50 micro M, suppresses interferon-gamma (INFγ) stimulated production of IL-8 and related cytokines by human keratinocytes [Stoof et al, supra]. These cytokines are thought to be responsible for the perpetuation of psoriasis lesions. The mechanism of DMF on IL-8 production may be via the NFβB pathway, since DMF causes nuclear accumulation of cytokine-induced NFκB1/p50 in human dermal fibroblast cells [Vandermeeren et al, *J. Invest. Dermatol.,* 116:124-130, (2001)]. Therefore, the pyridinium compounds of the present invention capable of interfering with IL-8 secretion in dermal cells are useful as anti-psoriasis agents.

In another embodiment, the amphiphilic pyridinium compound(s) of Table I is administered to a mammal for the treatment of rheumatoid arthritis and related inflammatory disorders. Rheumatoid arthritis, afflicting approximately 1% of the population, is a chronic multisystem disease of unknown cause, characterized by persistent inflammatory synovitis, principally in symmetrical peripheral joints [Lipsky, Rheumatoid arthritis, *Harrisons Principles of Internal Medicine,* 15$^{th}$ edition (eds, Braunwald et al) McGraw-Hill, Pubs., New York pp1929-1937, (2001)]. High basal levels of IL-8 are found in synovial fluid and in synovial cells [Troughton et al, *Br J. Pheumatol.,* 35:1244-51, (1996); and Hayashida et al, *Arthritis Res.,* 3:118-26, (2001)]. It has been proposed that IL-8 participates in synovial lesions at the earliest stages of rheumatoid disease [Takahashi et al, *Tohoku J. Exp. Med.,* 188:75-87, (1999)], and that symptoms coincide with increased synthesis of IL-8 [Kraan et al, *Arthritis Res.,* 3:65-71, (2001)]. The synthesis of IL-8 by synovial attracts ingress of peripheral monocytes [Hayashida et al, *Arthritis Res.,* 3:118-26, (2001)], as well as angiogenesis, possibly to support the chronic inflammatory state [Koch et al, *Arthritis Rheum.,* 44:31-40(2001)]. The mechanism of IL-8 synthesis by synovial cells involves the NFκB pathway (Morel et al, *Lab Invest.,* 81:1371-83, (2001)] and increases in IL-8 mRNA. Certain other categories of arthritis are also characterized by high levels of IL-8, including Behcet's disease [Ertenli et al, *Clin Exp. Pheumatol Suppl.,* 24:S37-41 (2001)], psoriasis [Konig et al, *Rheumatol Int.,* 17:(1)59-68, (1997)]. Therapy of rheumatoid arthritis by either methotrexate [Gao et al, *Z Rheumatol,* 57:95-100, (1998)] or aurothioglucose [Yoshida et al, *Int. Immunol.,* 11:151-8, (1999)] results in reduction of IL-8 levels in the affected joints. Therefore, the pyridinium compounds of the present invention capable of interfering with IL-8 secretion in synovial tissues are useful as therapeutics for the treatment of rheumatoid types of IL-8 related arthritis.

In yet another embodiment, the present invention provides a method for suppressing IL-8 secretion or production and a method for the treating IL-8 related diseases using one or more of the pyridinium salts shown in Table 2. Table 2 illustrates various pyridinium salts in the family of inhibitors of IL-8. In the following compounds of Table 2, X=anion, such as halide, mesylate, oxalate, etc. to form a acceptable salt.

TABLE 2
| Compound | |
|---|---|
| 25 | 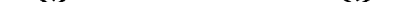 |
| 26 | 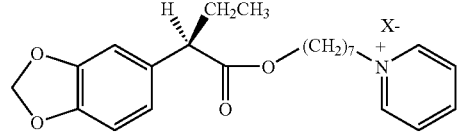 |
| 27 | 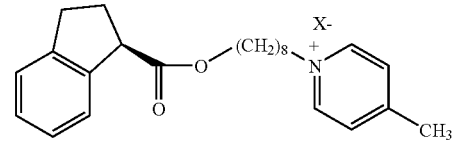 |
| 28 | 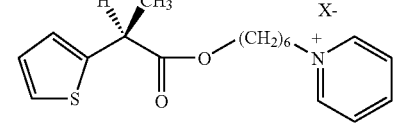 |
| 29 | 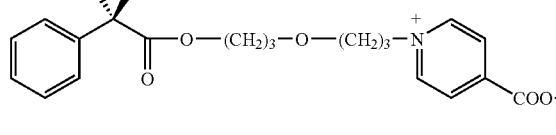 |
| 30 | 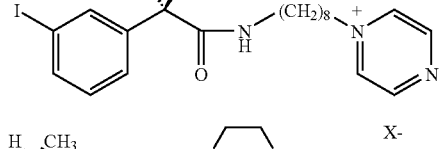 |
| 31 | 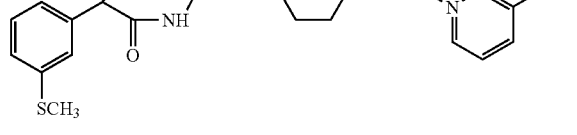 |
| 32 | 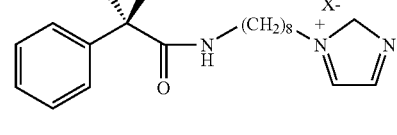 |
| 33 | 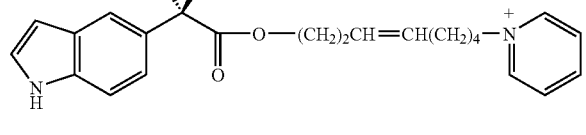 |
| 34 | 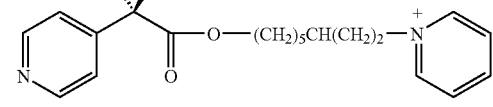 |

The present invention provides for both prophylactic and therapeutic methods of treating a mammal at risk for, susceptible to or diagnosed with an IL-8 related disease, such as cystic fibrosis. With regard to both prophylactic and therapeutic methods of treatment, such treatments may be specifically tailored or modified, based on knowledge obtained from the field of pharmacogenomics. "Pharmacogenomics," as used herein, includes the application of genomics technologies such as gene sequencing, statistical genetics, and gene expression analysis to drugs in clinical development and on the market. More specifically, the term refers the study of how a subject's genes determine his or her response to a drug (e.g., a subject's "drug response phenotype" or "drug response genotype"). Thus, another aspect of the invention provides methods for tailoring an individual's prophylactic or therapeutic treatment with the amphiphilic pyridinium compounds of the present invention according to that individual's drug response. Pharmacogenomics allows a clinician or physician to target prophylactic or therapeutic treatments to subjects who will most 5 benefit from the treatment and to avoid treatment of subjects who will experience toxic drug-related side effects.

In one aspect, the present invention provides a method for preventing a mammal in diseases associated with aberrant IL-8 expression or activity, by administering to the mammal a therapeutically effective amount of one or more amphiphilic pyridinium compound(s) of the present invention. Administration of the amphiphilic pyridinium compound(s) may occur prior to the manifestation of symptoms characteristic of IL-8 over-expression, such that the disease is prevented or, alternatively, delayed in its progression.

The term "therapeutically effective amount" as used herein, is that amount achieves at least partially a desired therapeutic or prophylactic effect in an organ or tissue. The amount of a pyridinium compound necessary to bring about prevention and/or therapeutic treatment of IL-8 related diseases or conditions is not fixed per se. An effective amount is necessarily dependent upon the identity and form of pyridinium compound employed, the extent of the protection needed, or the severity of the IL-8 related diseases or conditions to be treated.

Another aspect of the invention pertains to methods of modulating IL-8 expression or activity for therapeutic purposes. Accordingly, in an exemplary embodiment, the modulatory method of the invention involves contacting a cell with an amphiphilic pyridinium compound, such as MSR2481, that inhibits IL-8 secretion.

In conjunction with the prophylactic or therapeutic treatment, pharmacogenomics (i.e., the study of the relationship between an individual's genotype and that individual's response to a foreign compound or drug) may be considered. Differences in metabolism of therapeutics can lead to severe toxicity or therapeutic failure by altering the relation between dose and blood concentration of the pharmacologically active drug. Thus, a physician or clinician may consider applying knowledge obtained in relevant pharmacogenomics studies in determining whether to administer a amphiphilic pyridinium compound as well as tailoring the dosage and/or therapeutic regimen of treatment with a amphiphilic pyridinium compound.

Pharmacogenomics deals with clinically significant hereditary variations in the response to drugs due to altered drug disposition and abnormal action in affected persons. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare genetic defects or as naturally-occurring polymorphisms. For example, glucose-6-phosphate dehydrogenase deficiency (G6PD) is a common inherited enzymopathy in which the main clinical complication is haemolysis after ingestion of oxidant drugs (anti-malarials, sulfonamides, analgesics, nitrofurans) and consumption of fava beans.

One pharmacogenomics approach to identifying genes that predict drug response, known as a "genome-wide association," relies primarily on a high-resolution map of the human genome consisting of already known gene-related sites (e.g., a "bi-allelic" gene marker map which consists of 60,000-100,000 polymorphic or variable sites on the human genome, each of which has two variants). Such a high-resolution genetic map can be compared to a map of the genome of each of a statistically substantial number of subjects taking part in a Phase II/III drug trial to identify genes associated with a particular observed drug response or side effect. Alternatively, such a high resolution map can be generated from a combination of some ten-million known single nucleotide polymorphisms (SNPs) in the human genome. As used herein, a "SNP" is a common alteration that occurs in a single nucleotide base in a stretch of DNA. For example, a SNP may occur once per every 1000 bases of DNA. A SNP may be involved in a disease process. However, the vast majority of SNPs may not be disease associated. Given a genetic map based on the occurrence of such SNPs, individuals can be grouped into genetic categories depending on a particular pattern of SNPs in their individual genome. In such a manner, treatment regimens can be tailored to groups of genetically similar individuals, taking into account traits that may be common among such genetically similar individuals. Thus, mapping of the amphiphilic pyridinium compounds of the invention to SNP maps of patients may allow easier identification of these genes according to the genetic methods described herein.

Alternatively, a method termed the "candidate gene approach," can be utilized to identify genes that predict drug response. According to this method, if a gene that encodes a drug target is known (e.g., IL-8 gene), all common variants of that gene can be fairly easily identified in the population and it can be determined if having one version of the gene versus another is associated with a particular drug response.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and cytochrome P450 enzymes CYP2D6 and CYPZC19) has provided an explanation as to why some subjects do not obtain the expected drug effects or show exaggerated drug response and serious toxicity after taking the standard and safe dose of a drug. These polymorphisms are expressed in two phenotypes in the population, the extensive metabolizer and poor metabolizer. The prevalence of poor metabolizer phenotypes is different among different populations. For example, the gene coding for CYP2D6 is highly polymorphic and several mutations have been identified in poor metabolizers, which all lead to the absence of functional CYP2D6. Poor metabolizers of CYP2D6 and CYP2C19 quite frequently experience exaggerated drug response and side effects when they receive standard doses. If a metabolite is the active therapeutic moiety, poor metabolizers show no therapeutic response, as demonstrated for the analgesic effect of codeine mediated by its CYP2D6-formed metabolite morphine. The other extreme are the so called ultra-rapid metabolizers who do not respond to standard doses. Recently, the molecular basis of ultra-rapid metabolism has been identified to be due to CYP2D6 gene amplification.

Alternatively, a method termed the "gene expression profiling" can be utilized to identify genes that predict drug response. For example, the gene expression of an animal dosed with a drug (e.g., IL-8 secretion in response to a amphiphilic pyridinium compound of the present invention) can give an indication whether gene pathways related to toxicity have been turned on.

Information generated from more than one of the above pharmacogenomics approaches can be used to determine appropriate dosage and treatment regimens for prophylactic or therapeutic treatment an individual. This knowledge, when applied to dosing or drug selection, can avoid adverse reactions or therapeutic failure and thus enhance therapeutic or prophylactic efficiency when treating a mammal with an amphiphilic pyridinium compound.

The invention is further directed to pharmaceutical compositions comprising one or more amphiphilic pyridinium compound(s) of the present invention and a pharmaceutically acceptable carrier.

As used herein the language "pharmaceutically acceptable carrier" is intended to include any and all solvents, solubilizers, fillers, stabilizers, binders, absorbents, bases, buffering agents, lubricants, controlled release vehicles, diluents, emulsifying agents, humectants, lubricants, dispersion media, coatings, antibacterial or antifungal agents, isotonic and absorption delaying agents, and the like, compatible with pharmaceutical administration. The use of such media and agents for pharmaceutically active substances is well-known in the art. Except insofar as any conventional media or agent is incompatible with the active compound, use thereof in the compositions is contemplated. Supplementary agents can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine; propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the injectable composition should be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the requited particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a fragment of a CRTP or an anti-CRTP antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can-also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose; a disintegrating agent such as alginic acid, Primogel, or corn starch; a lubricant such as magnesium stearate or Stertes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from a pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the bioactive compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the therapeutic moieties, which may contain a bioactive compound, are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from e.g. Alza Corporation and Nova Pharmaceuticals, Inc. Liposomal suspensions (including liposomes targeted to infected cells with monoclonal antibodies to viral antigens) can also be used as pharmaceutically acceptable carriers.

It is especially advantageous to formulate oral or parenteral compositions in dosage unit form for ease of administration and uniformity of dosage. Dosage unit form as used herein includes physically discrete units suited as unitary dosages for the subject to be treated; each unit contains a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices are preferred. While compounds that exhibit toxic side effects maybe used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that includes the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

The present invention is further illustrated by the following examples which should not be construed as limiting. The contents of all references, patents and published patent applications cited throughout this application, as well as the Figures and Tables are incorporated herein by reference.

EXAMPLE 1

Identification of Amphiphilic Pyridinium Salts that Suppress IL-8 Section in IB-3 CF Lung Epithelial Cells 1(a). Cells and Culture Methods The CF lung epithelial cells IB3 and S9 have been previously described [Zeitlin et al., 1991; Eidelman et al., 2001a)]. Both IB2 and S9 cells were grown in serum-free LHC-8 medium (Biofluids), formulated without gentimycin. CF tracheal epithelial cells (2CFTE29o-) were obtained from University of Vermont. The latter cells were grown in EMEM (Biofluids), supplemented with 10% fetal bovine serum (FBS) and 1% Penicillin G-Streptomycin.

1(b). Default Conditions and Controls for Screening Paradigm

Initial assays for dug effects in the screening paradigm were performed in duplicate at 10, 3, 1, and 0.3 µM concentrations on IB-3 cells grown in 96 well microtiter plates. Each individual plate contained IB-3 and IB-3/S9 cells to set the boundary conditions of the assay. CPX and DAX, 5 µM each, were included in separate wells as positive controls. "Hits" in the screen were chosen on the basis of at least a 50% reduction in constitutive IL-8 secretion. Following a positive retest, candidate compounds were taken off-line for more detailed analysis under the exact same assay conditions. Many of the compounds we have screened need solvents such as DMSO or ethanol for initial solubility. In most circumstances we use a maximum final solvent concentration of 0.1% DMSO or 0.01% ETOH. Higher concentrations of DMSO substantially suppress IL-8 secretion. The solvent control, which at the concentration picked minimally deviates from medium alone, is then used as a basis for 100% activity.

1(c). Detection of IL-8 Culture Fluids from Screening Samples

The details of this assay have been described in a previous publication (Eidehman et la., 2001 a). Briefly, IB-3 cells are grown in 96 well microtiter plates to 80% confluency. Drugs, diluted in LHC-8 medium at the given concentrations, are added, and the cells allowed to incubate for an additional 24 hours. To initiate the experiment, cells are washed with fresh LHC-8 medium, and then incubated for an additional 16 hours in the same medium supplemented with drug. At the end of the time period, the supernatant solutions are collected and assayed for IL-8 by and ELISA assay. Alternatively, the samples are immediately frozen at −80° C. No quantitative differences have been noted when both paradigms were applied to the same sample handled in either manner. The IL-8 ELISA assay was assembled from bulk materials purchased from R&D, and performed exactly according to the manufacturers specifications. To detect possible drug toxicity on cells, as well as normalize to total cells per well, we measure the double stranded DNA content of cells attached to the plate after removal of supernatant solutions for IL-8 assay. Cells remaining on the plate are then fixed with 10% formalin for 30 minutes at room temperature before being incubated with propidium iodide (kit from Boehringer Mannheim). Propidium iodide content in each well is then measured with an automated fluorescence plate reader (FLUOstar Optima, MBG Lab Technologies). Final IL-8 data are calculated as a ratio of secreted IL-8 to DNA for each well. On occasion, cell proliferation assays are also carried out using the XTT assay (Roche).

Figure 2:
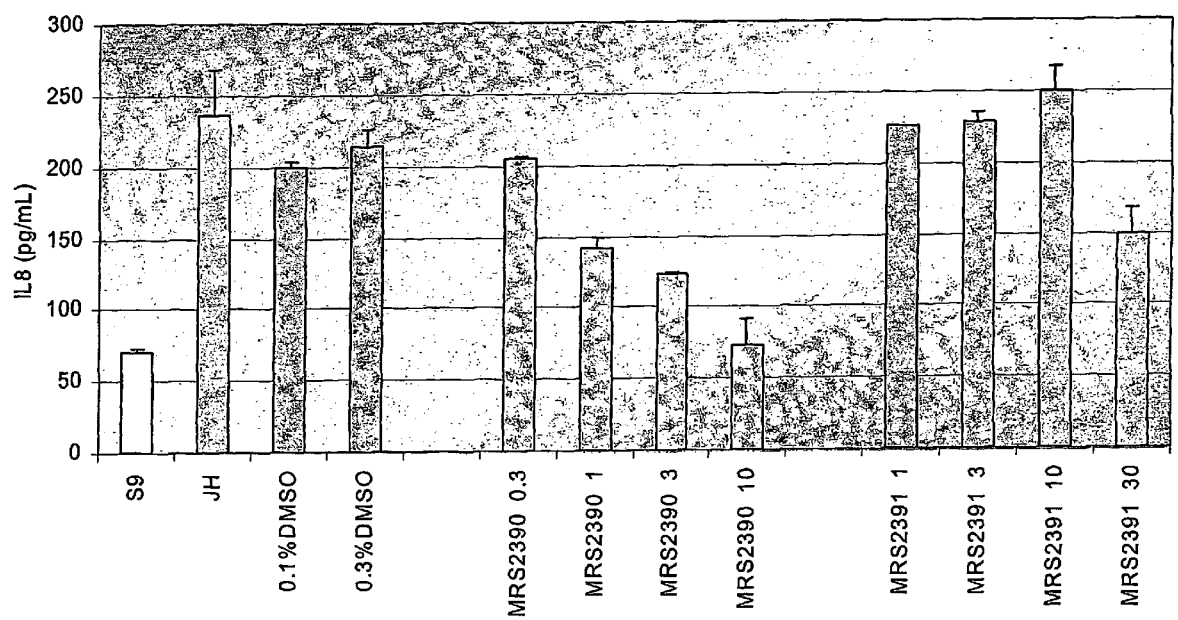
FIG. 2 illustrates suppression of IL8 secretion by different concentrations of amphiphilic compounds of the MRS2390 and MRS2391.

From library screening, there are identified a series of amphiphilic pyridinium salts that suppressed spontaneouslyelevated IL-8 secretion in IB-3 CF lung epithelial cells. Representative data are shown in FIGS. 1 and 2 (in both figures, JH is the un-treated IB-3 cells). The $IC_{50}$ values are given in Table 3 below. Table 3. Structures and potencies of pyridinium compounds as inhibitors of IL-8 secretion from CF IB-3 cells.

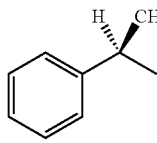

Compounds 1–19 (Formula I)

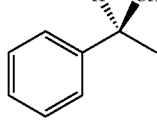

Compounds 20–22 (Formula II)

| Compound | $R_1$ | n | $R_2$ | $IC_{50}$ |
|---|---|---|---|---|
| 1 MRS 2572 | 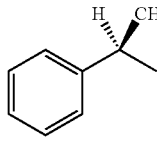 | 4 | H | >30 |
| 2 MRS 2573 | 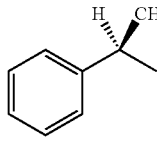 | 6 | H | >30 |
| 3 MRS 2481 | 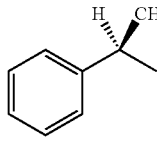 | 8 | H | 0.35 ± 0.1 |
| 4 MRS 2574 | 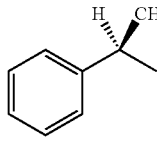 | 10 | H | 2.52 ± 0.39 |
| 5 MRS 2485 | 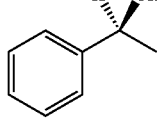 | 8 | H | >25 |
| 6 MRS 2515 | 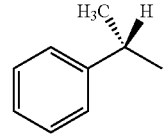 | 8 | H | >30 |
| 7 MRS 2480 | 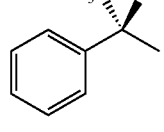 | 8 | H | 12 ± 0.8 |

-continued
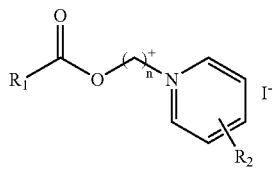
Compounds 1–19 (Formula I)
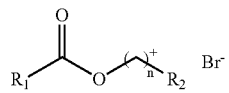
Compounds 20–22 (Formula II)
| Compound | R₁ | n | R₂ | IC₅₀ |
|---|---|---|---|---|
| 8 MRS 2591 | (phenyl-CH(H)(C₂H₅)-) | 8 | H | 3.16 ± 0.52 |
| 9 MRS 2506 | (phenyl-CH(H)(OCH₃)-) | 8 | H | >30 |
| 10 MRS 2507 | (benzyl-O-CH(CH₃)-) | 8 | H | >30 |
| 11 MRS 2513 | (phenyl-) | 8 | H | >30 |
| 12 MRS 2514 | (phenyl-CH₂-C(OH)(H)(CH₃)-) | 8 | H | >30 |
| 13 MRS 2516 | (phenyl-CH₂-C(H)(OH)(CH₃)-) | 8 | H | >30 |
| 14 MRS 2590 | (4-isobutylphenyl-CH(CH₃)₂-) | 8 | H | ND |
| 15 MRS 2390 | (4-isobutylphenyl-CH(H)(CH₃)-) | 8 | H | 2.2 ± 0.8 |

-continued
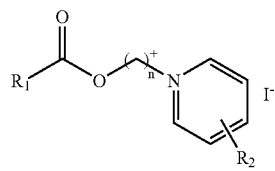
(Formula I)
Compounds 1–19
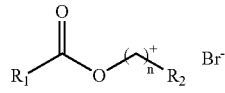
(Formula II)
Compounds 20–22
| Compound | R₁ | n | R₂ | IC$_{50}$ |
|---|---|---|---|---|
| 16 MRS 2517 | (CH₃)₃COCONH–C₆H₄–CH(CH₃)₂ | 8 | H | 4.6 ± 0.9 |
| 17 MRS 2518 | CF₃COOH·H₂N–C₆H₄–CH(CH₃)₂ | 8 | H | >30 |
| 18 MRS 2589 | (CH₃)₂CHCH₂–C₆H₄–CH(CH₃)₂ | 8 | 3-CONH₂ | 5.56 ± 0.98 |
| 19 MRS 2421 | (CH₃)₂CHCH₂–C₆H₄–*CH(CH₃) | 8 | p-CH₂CH₂CH₃ | 3.3 ± 0.5 |
| 20 MRS 2423 | (CH₃)₂CHCH₂–C₆H₄–*CH(CH₃) | 8 | p-(CH₂)₂—OH | 18 ± 0.9 |
| 21 MRS 2422 | (CH₃)₂CHCH₂–C₆H₄–*CH(CH₃) | 8 | N-methylmorpholinium | 24 ± 1.0 |
| 22 MRS 2391 | (CH₃)₂CHCH₂–C₆H₄–*CH(CH₃) | 8 | (CH₃)₂CHCH₂–C₆H₄–*CH(CH₃)COO— | >30 |

The pyridinium salts incorporate an anionic counter-ion, which can be any pharmaceutically acceptable anion. The structure activity relationship follows a precise pattern. The mechanism involves at least one specific interaction with a target molecule (i.e. a macromolecular "receptor"). Depending on minor structural changes, the potencies can vary between inactive and active at a submicromolar concentration.

The compounds synthesized are amphiphilic derivatives, consisting of a hydrophobic ester moiety and a hydrophilic pyridinium moiety linked through an alkyl chain of 4 to 10 carbons (1- 4). Among these compounds, Compound 3, an (R)-1-phenylpropionic acid ester, showed strongest inhibition to IL-8 secretion with an $IC_{50}$ of 0.35 μM. A hydrophobic moiety present on the pyridinium derivatives displayed highly specific structural requirements in suppression of IL-8 production.

The enantiomer of Compound 3, Compound 5, was much less active in effect on IL-8 production. Thus, there is a stereoselectivity of action of >70-fold in favor of the (R)-isomer. This is characteristic of binding to a specific site on a macromolecule. Replacement of the methyl-hydrogen of Compound 5 with a hydroxyl group, leading to Compound 6, failed to restore the activity. The length of the n-alkyl chain can be varied. Removal of the α-methyl group of the most potent analogue (i.e. resulting in Compound 7), thus removing the chiral center of the molecule, led to a 34-fold loss of potency. Replacement of this methyl group by methoxy eliminated the activity (Compound 8). Isomerization of the ester group of Compound 8, leading to Compound 9, failed to restore the activity. Removal of two carbons at the α-position of Compound 3, which resulted in Compound 11, significantly reduced the activity of Compound 3. The stereoselectivity of the effects of two enantiomeric 1-hydroxy-2-phenylethyl derivatives (Compound 12 and Compound 13) could not be assessed, since no activity was evident. Substitution at the p-position of the phenyl ring with a branched alkyl group Compound 15 resulted in a 6-fold loss of potency. The substitution of the p-position of the phenyl ring in two racemic derivatives indicated that the introduction of a urethane group in Compound 16 was possible with retention of the activity, while the small hydrophilic p-amino group in Compound 17 eliminated activity.

Addition of a p-substituent of the pyridinium moiety of Compound 15 led to either retention of potency (ethyl) or an 8-fold loss of potency (2-hydroxyethyl) relative to Compound 13. The pyridinium moiety could be replaced with an N-methylmorpholino moiety (Compound 21) with only an 11-fold loss of potency, while the replacement with an uncharged moiety identical to the ester side of the molecule to give a dimeric structure (Compound 22) eliminated the activity. Thus, the activity is associated with the presence of a positively-charged ammonium group.

EXAMPLE 2

Synthesis of Representative Pyridinium Salts 2 (a). Materials and Instrumentation Reagents and solvents were purchased from Sigma-Aldrich (St. Louis, Mo.).

$^1$H NMR spectra were obtained with a Varian Gemini-3000 spectrometer (300 MHz) with $D_2O$, $CDCl_3$, $CD_3OD$, and $DMSO-d_6$ as a solvent. The chemical shifts were expressed as ppm downfield from TMS. Purity of compounds was checked with a Hewlett-Packard 1090 HPLC apparatus equipped with an SMT OD-5-60 RP-C18 analytical column (250×4.6 mm; Separation Methods Technologies, Inc., Newark, Del.) in two solvent systems.

System A: linear gradient solvent system: 0.1 M TEAA/$CH_3CN$ from 95/5 to 40/60 in 20 min.; the flow rate was 1 ml/min.

System B: linear gradient solvent system: 5 mM TBAP/$CH_3CN$ from 80/20 to 40/60 in 20 min.; the flow rate was 1 ml/min.

TLC analysis was carried out on aluminum sheets pre-coated with silica gel $F_{254}$ (0.2 mm) from Aldrich.

2 (b) General Procedure for the Synthesis of the Compounds 1-14 and 16-18:

(i) Synthesis R-8-Bromo-n-octyl α-methyl-2-phenylacetate

R-(-)-2-Phenylpropinic acid (mg 210, 1.4 mmol) and 1,8 diBromo-octane (ml 0.26, 1.4 mmol) were put in a 5 cc round bottom flask with a methanolic solution of Benzyltrimethylammonium hydroxide (ml 0.635, 40%). Tetrabutylammonium iodide (mg 14, 0.038 mmol) was added and the mixture was stirred for 3 days. The mixture was poured in water (30 ml), and the aqueous solution was extracted with Ethyl acetate (10 ml×3). The organic phase was dried over $Na_2SO_4$, filtered and concentrated. The residue was purified using preparative thin layer chromatography (silica gel, eluting with petroleum ether: ethyl acetate, 20:1) obtaining mg 181 of pure R-8-Bromo-n-octyl α-methyl-2-phenylacetate (yield 38%).

$^1$H NMR ($CDCl_3$, 300 MHZ) δ 7.34-7.24 (m, 5H), 4.05 (t, J=6.3 HZ, 2H), 3.70 (q, J=6.9 Hz), 3.41 (t, J=6.3 Hz, 2H), 1.90-1.80 (m, 1H), 1.56-1.37 (m, 7H), 1.35-1.20 (m, 6H).

(ii) Synthesis R-8-Iodo-n-octyl α-methyl-2-phenylacetate

R-8-Bromo-n-octyl α-methyl-2-phenylacetate, (200 mg, 0.58 mmol) was dissolved in Acetone (5 ml) and NaI (mg 90, mmol 10.6) was added. The mixture was stirred at R.T. overnight. The solvent was concentrated and water (20 ml) was added, and the aqueous phase was extracted with Ethyl acetate (10 ml×3). The organic phase was dried over $Na_2SO_4$ filtered and concentrated. The product was sufficiently pure to be used without further purification.

$^1$H NMR ($CDCl_3$, 300 MHZ) δ 7.32-7.24 (m, 5H), 4.05 (t, J=6.3 HZ, 2H), 3.70 (q, J=6.9 Hz), 3.18 (t, J=6.3 Hz, 2H), 1.84-1.79 (m, 1H), 1.56-1.37 (m,7H), 1.35-1.23 (m, 6H).

(iii) Synthesis R-8-Pyridinium-n-octyl α-methyl-2-phenylacetate iodide (Compound 3)

R-8-Iodo-n-octyl α-methyl-2-phenylacetate (100 mg, 0.26 mmol) was dissolved in acetone (ml 10) and pyridine (ml 0.3) was added. The solution was stirred at 50° C. for three days. The solvent was evaporated and the residue dissolved in water (20 ml). The aqueous phase was washed with ether (10×3) and lyophilized to give mg 54 of pure Compound 3 (yield 45%).

$^1$H NMR ($D_2O$, 300 MHZ) δ 8.80 (d, J=6.6 Hz, 2H), 8.57 (t, J=9 Hz, 1H), 8.09 (t, J=6.9 Hz, 2H), 7.45-7.31 (m, 5H), 4.53 (t, J=7.2 Hz, 2H), 4.19-4.05 (m, 2H), 3.88 (q, J=6.9 Hz, 1H), 1.94-1.88 (m,2H), 1.61-1.56 (m,2H), 1.49-1.42 (m, 7H), 1.27-1.23 (m, 4H).

(iv) Synthesis R-8-Pyridinium-n-butyl α-methyl-2-phenylacetate iodide (Compound 1)

$_1$H NMR ($D_2O$, 300 MHZ) δ 8.67 (d, J=6.6 Hz, 2H), 8.57 (t, J=9 Hz, 1H), 8.07 (t, J=6.9 Hz, 2H), 7.43-7.31 (m, 5H), 4.45 (t, J=7.2 Hz, 2H), 4.29-4.09 (m, 2H), 3.90 (q, J=6.9 Hz, 1H), 1.92-1.82 (m, 2H), 1.72-1.65 (m, 2H), 1.49 (d, J=7.2 Hz, 3H).

(v) Synthesis R-8-Pyridinium-n-hexyl α-methyl-2-phenylacetate iodide (Compound 2)

¹H NMR (D₂O, 300 MHZ) δ 8.81 (d, J=6.6 Hz,2H), 8.57 (t, J=9 Hz, 1H), 8.08 (t, J=6.9 Hz, 2H), 7.45-7.30 (m, 5H), 4.3 (t, J=7.2 Hz, 2H), 4.21-4.12 (m, 2H), 3.89 (q, J=6.9 Hz, 1 H), 1.94-1.86 (m, 2H), 1.62-1.55 (m, 2H), 1.48 (d, J=7.2 Hz, 3H), 1.27-1.22 (m, 4H).

(vi) Synthesis R-8-Pyridinium-n-decyl α-methyl-2-phenylacetate iodide (Compound 4)

¹H NMR (D₂O, 300 MHZ) δ 8.89-8.87 (m, 2H), 8.61-8.57 (m, 1H), 8.11-8.07 (m, 2H), 7.33-7.14 (m, 5H), 4.69-4.55 (m, 2H), 4.09-3.92 (m, 2H), 3.66 (q, J=6.9 Hz, 1H), 2.02-1.92 (m, 2H), 1.49-1.08 (m, 17H).

(vii) Synthesis S-8-Pyridinium-n-octyl α-methyl-2-phenylacetate iodide (Compound 5)

¹H NMR (D₂O, 300 MHZ) δ 8.80 (d, J=6.6 Hz, 2H), 8.57 (t, J=9 Hz, 1H), 8.09 (t, J=6.9 Hz, 2H), 7.45-7.31 (m, 5H), 4.53 (t, J=7.2 Hz, 2H), 4.19-4.05 (m, 2H), 2.88 (q, J=6.9 Hz, 1H), 1.94-1.88 (m, 2H), 1.61-1.56 (m, 2H), 1.49-1.42 (m, 7H), 1.27-1.23 (m, 4H).

(viii) Synthesis R-8-Pyridinium-n-octyl α-hydroxy-α-methyl-2-phenylacetate iodide (Compound 6)

¹H NMR (D₂O, 300 MHZ) δ 8.84 (d, J=6.6 Hz, 2H), 8.56 (t, J=9 Hz, 1H), 8.08 (t, J=6.9 Hz, 2H), 7.57-7.39 (m, 5H), 4.60 (t, J=7.2 Hz, 2H), 4.15 (t, J=4.2 Hz, 2H), 2.02-1.96 (m, 2H), 1.83 (s, 3H0), 1.59-1.55 (m, 2H), 1.24-1.17 (m, 8H).

(ix) Synthesis 8-Pyridinium-n-octyl propionate iodide (Compound 7)

¹H NMR (D₂O, 300 MHZ) δ 8.88 (d, J=6.6 Hz, 2H), 8.66 (t, J=9 Hz, 1H), 8.14 (t, J=6.9 Hz, 2H), 7.47-7.38 (m, 5H), 4.55 (t, J=7.2 Hz, 2H), 4.25 (t, J=4.2 Hz, 2H), 3.85 (s, 2H), 2.12-1.98 (m, 2H), 1.56-1.37 (m, 4H), 1.30-1.19 (m, 6H).

(x) Synthesis R-8-Pyridinium-n-octyl α-ethyl-2-phenylacetate iodide (Compound 8) ¹H NMR (D₂O, 300MHZ) δ 9.31 (d, J=6.6 Hz, 2H), 8.49 (t, J=9 Hz, 1H), 8.10 (t, J=6.9 Hz, 2H), 7.31-7.22 (m, 5H), 4.39 (t, J=7.2 Hz, 2H), 4.06-4.01 (m, 2H), 3.48-3.41 (m, 1H), 2.11-1.90 (m, 3H), 1.84-1.74 (m, 1H), 1.61-1.46 (m, 4H), 1.32-1.20 (m, 6H), 0.89 (t, J=7.2 Hz, 2H).

(xi) Synthesis S-8-Pyridinium-n-octyl α-methoxy-2-phenylacetate iodide (Compound 9)

¹H NMR (D₂O, 300 MHZ) δ 8.82 (d, J=6.6 Hz, 2H), 8.57 (t, J=9 Hz, 1H), 8.09 (t, J=6.9 Hz, 2H), 7.48-7.42 (m, 5H), 4.59 (t, J=7.2 Hz, 2H), 4.29-4.10 (m, 3H), 3.41 (s, 3H), 2.02-1.88 (m, 2H), 1.61-1.52 (m, 2H), 1.29-1.12 (m, 8H).

(xii) Synthesis S-8-Pyridinium-n-octyl α-benzyloxy-2-propionate iodide (Compound 10)

¹H NMR (D₂O, 300 MHZ) δ 8.81 (d, J=6.6 Hz, 2H), 8.57 (t, J=9 Hz, 1H), 8.07 (t, J=6.9 Hz, 2H), 7.45-7.40 (m, 5H), 4.62-4.58 (m, 4H), 4.25 (q, J=6.9 Hz, 1H), 4.18 (t, J=7.2 Hz, 2H), 2.02-1.94 (m, 2H), 1.72-1.60 (m, 2H), 1.40 (d, J=7.2 Hz, 3H), 1.38-1.26 (m,8H).

(xiii) Synthesis 8-Pyridinium-n-octyl benzoate iodide (Compound 11)

¹H NMR D₂O, 300 MHZ) δ 8.81 (d, J=6.6 Hz, 2H), 8.51 (t, J=9 Hz, 1H), 8.03 (m, 4H), 7.65-7.55 (m, 1H), 7.56-7.51 (m, 2H), 4.59-4.55 (m, 2H), 4.34 (t, J=7.2 Hz, 2H), 4.05 (q, J=6.9 Hz, 1H), 2.02-1.94 (m, 2H), 1.78-1.74 (m, 2H), 1.62-1.26 (m,8H).

(xiv) Synthesis R-8-Pyridinium-n-octyl 2-hydroxy-3-phenylpropionate iodide (Compound 12) and S-8-Pyridinium-n-octyl 2-hydroxy-3-phenylpropionate iodide (Compound 13)

¹H NMR (D₂O, 300 MHZ) δ 8.80 (d, J=6.6 Hz, 2H), 8.57 (t, 3-9 Hz, 1H), 8.09 (t, J=6.9 Hz, 2H), 7.38-7.22 (m, 5H), 4.65 (t, J=7.2 Hz, 2H), 4.44 (q, J=6.8 Hz, 1H), 4.14 (t, J=7.2 Hz, 2H), 3.18-3.02 (m, 2H), 1.95-1.82 (m, 2H), 1.69-1.62 (m,2H), 1.45-1.15 (m, 8H).

(xv) Synthesis 8-Pyridinium-n-octyl α-methyl-2-[4-)N-Boc amino)phenyl]acetate iodide (Compound 16)

¹H NMR (D₂O, 300 MHZ) δ 8.82 (d, J=6.6 Hz, 2H), 8.57 (t, J-9 Hz, 1H), 8.08 (t, J=6.9 Hz, 2H), 7.38-7.31 (m, 4H), 4.63 (t, J=7.2 Hz, 2H), 4.29-4.20 (m, 1H), 4.18-4.02 (m, 1H),3.88 (q, J=6.9 Hz, 1H), 1.98-1.88 (m,2H), 1.61-1.56 (m, 13H), 1.27-1.23 (m, 9H).

(xvi) Synthesis 8-Pyridinium-n-octyl α-methyl-2-[4-ammonium-phenyl]acetate iodide (Compound 17)

¹H NMR (D₂O, 300 MHZ) δ 8.85 (d, J=6.6 Hz, 2H), 8.57 (t, J-9 Hz, 1H), 8.08 (t, J=6.9 Hz, 2H), 7.49-7.35 (m, 4H), 4.62 (t, J=7.2 Hz, 2H), 4.14 (t, J=7.2 Hz, 2H), 3.95 (q, J=6.9 Hz, 1H), 1.98-1.88 (m, 2H), 1.61-1.49 (m, 5H), 1.31-1.25 (m, 8H).

(xvii) Synthesis 8-(3-carboxyamido-pyridinium)-n-octylα-methyl-2-(4[2-methylpropyl]benzene)-acetate iodide (Compound 18)

¹H NMR (D₂O, 300 MHZ) δ 10.21 (s, 1H), 9.16 (d, J-9 Hz, 1H), 8.98 (d, J=6.6 Hz, 2H), 8.58 (s, 1H), 8.19 (t, J=6.9 Hz, 2H), 7.21-7.08 (m, 4H), 6.53 (s, 1H), 4.88 (t, J=7.2 Hz, 2H), 4.07-4.03 (m, 2H), 3.70 (q, J=6.8 Hz, 1H), 2.44 (d, J=9 Hz, 2H), 2.18-2.02 (m, 2H), 1.85-1.72 (m, 5H), 1.57-1.26 (m, 9H), 0.89 (d, J=6.6 Hz, 6H).

2 (c). General Procedure for the Synthesis of the Compounds 15 and 19-22

(i) Synthesis S,S-1.8-di((α-methyl 2-(4-[2-methylpropyl]phenyl acetoxy)-n-octane (Compound 22)

S-α-methyl-2-(4-[2-methylpropyl]benzene)acetic acid (Aldrich Chemical Co., 206 mg, 1 mmol), 1,8-dibromooctane (Aldrich Chemical Co., 0.184 mL)were combined. A methanolic solution of benzyltriethylammonium methoxide (453 mg, 40%) and tetrabutyl ammonium iodide (10 mg) were added. The mixture was stirred at room temperature for 3 days. The product (HS III-93B, 167 mg., 0.42 mmol, 42% yield) was isolated using preparative thin layer chromatography (silica gel, eluting with hexanes:ethyl acetate, 20:1). A minor product, a dimeric molecule (HS III-93 C), was also isolated (34 mg, 7%).

¹H NMR (CDCl₃, 300 MHZ) δ 7.20 (d, J=7.8 Hz, 2H), 7.09 (d, J=7.8 Hz, 2H), 4.05 (t, J=6.3 Hz, 2H), 3.70 (q, J=6.9 Hz), 2.45 (d, J=7.2 Hz, 2H), 1.89-1.80 (m, 1H), 1.57-1.48 (m, 5H), 1.26-1.20 (m, 4H), 0.90 (d, J=6.6 Hz, 6H).

(ii) Synthesis of S-8-Pyridinium-n-octyl α-methyl-2-(4-[2-methylpropyl]benzeneacetate bromide (Compound 15)

S-8-Bromo-n-octyl α-methyl-2-(4-[2-methylpropyl]benzene)acetate (35 mg, 0.088 mmol) and pyridine (0.2 ml, 2.5 mmol) were dissolved in acetone (3 ml). Tetrabutyl ammonium iodide (10 mg) was added, and the mixture was stirred for 2 days at 50° C. Acetone was removed in vacuum. The product (HS IV-3, 16 mg, 0.035 mmol, 40% yield) was isolated using preparative thin layer chromatography (silica gel, eluting with chloroform:methano, 5:1).

¹H NMR (CD₃OD, 300 MHZ) δ 0.02 (d, J=6.6 Hz, 2H), 8.59 (t, J=9 Hz, 1H), 8.09 (t, J=6.9 Hz, 2H), 7.19 (d, J=7.8 Hz, 2H), 7.09 (d, J=7.8 Hz, 2H), 4.62 (t, J=7.2 Hz, 2H), 4.10-4.01 (m, 2H), 3.70 (q, J=6.9 Hz, 1H), 2.45 (d, J=7.2 Hz, 2H), 2.03-1.98 (m, 2H), 1.87-1.78 (m, 1H), 1.59-1.51 (m, 2H), 1.43 (d, J=7.2 Hz, 3H), 1.33-1.25 (m, 8H), 0.90 (d, J=6.6 Hz, 6H).

(iii) Synthesis of S-8-(4-n-Prolpylpyridinium)-n-octyl α-methyl-2-(4-[2-methylpropyl]benzene)acetate bromide (Compound9)

S-8-Bromo-n-octyl α-methyl-2-(4-[2-methylpropyl]benzene)acetate (35 mg, 0.088 mmol) and 4-n-propylpyridine (0.2 ml) were dissolved in acetone (3 ml). Tetrabutyl ammonium iodide (5 mg) was added, and the mixture was stirred for 2 days at 50° C. Acetone was removed in vacuum. The product (HS IV-3, 16 mg, 0.028 mmol, 35% yield) was isolated using preparative thin layer chromatography (silica gel, eluting with chloroform:methanol, 5:1).

$^1$H NMR(CD$_3$OD, 300MHZ) δ 9.32(d, J=6.6Hz,2H),7.84 (d, J=6.3 Hz,2H), 7.19 (d, J=7.8 Hz, 2H), 7.09 (d, J=7.8 Hz, 2H), 4.91 (t, J=7.2 Hz, 2H), 4.02 (t, J=7.2 Hz, 2H), 3.70 (q, J=6.9 Hz, 1H), 3.39-3.34 (m, 2H), 2.86 (t, J=7.2 Hz, 2H), 2.45 (d, J=7.2 Hz, 2H), 2.03-1.98 (m, 2H), 1.87-1.64 (m, 3H), 1.56-1.30 (m, 5H), 1.33-1.25 (m, 8H), 1.01 (t, J=7.2 Hz, 2H), 0.90 (d, J=6.6 Hz, 6H).

(iv) Synthesis of S-8-(4-2-hydroxy-ethyl)pyridinium)-n-octyl α-methyl-2-(4-[2-methylpropyl]benzene)acetate bromide (Compound 20)

$^1$H NMR (CDCl$_3$, 300 NMZ) δ 8.86 (d, J=6.6 Hz, 2H), 7.98 (d, J=6.3 Hz, 2H), 7.19 (d, J=7.8 Hz, 2H), 7.09 (d, J=7.8 Hz, 2H), 4.69 (t, J=7.2 Hz, 2H), 4.05-3.92 (m, 3H), 4.62-4.59 (m, 1H), 3.19-3.10 (m, 2H), 2.86 (t, J=7.2 Hz, 1H), 2.45 (d, J=7.2 Hz, 2H), 2.03-1.98 (m, 2H), 1.49-1.25 (m, 14H), 0.90 (d, J=6.6 Hz, 6H).

(v.) Synthesis of S-8-[N-Methylmorpholinium-n-octyl α-methyl-2-(4]2-methylpropyl]benzene)acetate bromide (Compound 21)

$^1$H NMR (CDCl$_3$, 300 MHZ) δ 7.19 (d, J=7.8 Hz, 2H), 7.09 (d, J=7.8 Hz, 2H), 4.13-3.98 (m, 6H), 3.89-3.78 (m, 4H), 3.71-3.55 (m, 6H), 3.40-3.24 (m, 2H), 2.45 (d, J=7.2 Hz, 2H), 1.86-1.26 (m, 13H), 1.02 (t, J=7.2Hz, 2), 0.90 (d, J=6.6 Hz, 6H).

The examples of the synthetic steps are illustrated as follows:

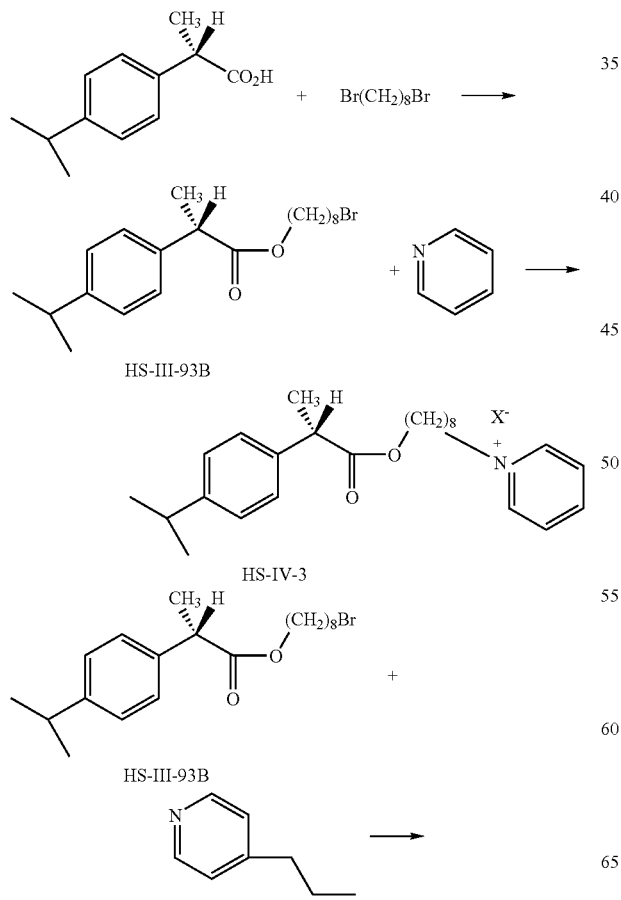

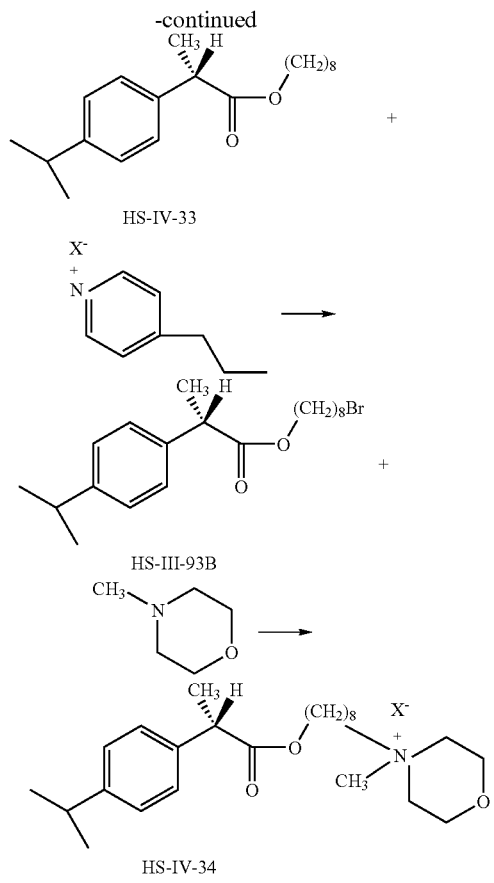

The preferred embodiments of the compounds and methods of the present invention are intended to be illustrative and not limiting. Modifications and variations can be made by persons skilled in the art in light of the above teachings. Therefore, it should be understood that changes maybe made in the particular embodiments disclosed which are within the scope of what is described as defined by the appended claims.

What is claimed is:

1. An amphiphilic pyridinium compound having a structure:

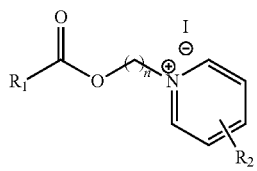

wherein, R$_1$ is selected from the group consisting of:

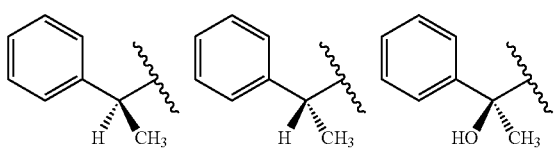

and R$_2$ is selected from the group consisting of H and 3-CONH$_2$, and n is an integer between 8 and 10.

2. The amphiphilic pyridinium compound of claim 1, wherein R$_1$ is

[structure: phenyl-CH(CH$_3$)- with H]

and R$_2$ is H, and n is 8.

3. The amphiphilic pyridinium compound of claim 1, wherein R$_1$ is

[structure: phenyl-CH(CH$_3$)- with H]

and R$_2$ is H, and n is 8.

4. The amphiphilic pyridinium compound of claim 1, wherein R$_1$ is

[structure: phenyl-CH(CH$_3$)- with H]

and R$_2$ is H, and n is 10.

5. The amphiphilic pyridinium compound of claim 1, wherein R$_1$ is

[structure: phenyl-CH(C$_2$H$_5$)- with H]

and R$_2$ is H, and n is 8.

6. The amphiphilic pyridinium compound of claim 1, wherein R$_1$ is

[structure: phenyl-CH(CH$_3$)- with H]

and R$_2$ is H, and n is 8.

7. The amphiphilic pyridinium compound of claim 1, wherein R$_1$ is

[structure: tBuO-C(O)-NH-C$_6$H$_4$-CH(CH$_3$)-]

and R$_2$ is H, and n is 8.

8. The amphiphilic pyridinium compound of claim 1, wherein R$_1$ is

[structure: iBu-C$_6$H$_4$-CH(CH$_3$)-]

and R$_2$ is 3-CONH$_2$, and n is 8.

9. The amphiphilic pyridinium compound of claim 1, wherein $R_1$ is

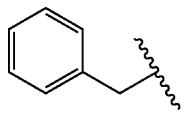

and $R_2$ is H, and n is 8.

10. An amphiphilic pyridinium compound having a structure:

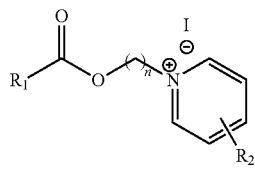

wherein $R_1$ is selected from the group consisting of:

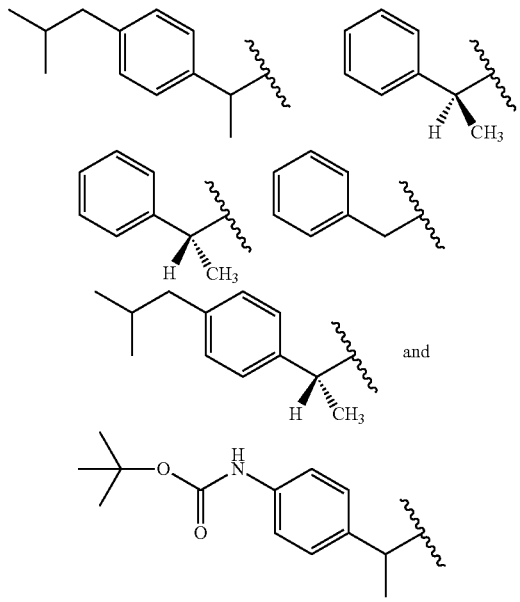

and $R_2$ is selected from the group consisting of H and 3-$CONH_2$, and n is an integer between 8 and 10.

11. A pharmaceutical composition comprising an amphiphilic pyridinium compound of claim 10, and a pharmaceutically acceptable carrier.

12. The pharmaceutical composition of claim 11, wherein said amphiphilic pyridinium compound is

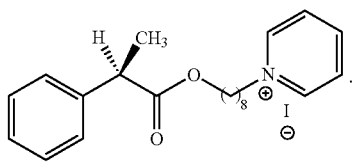

13. The pharmaceutical composition of claim 11, wherein said amphiphilic pyridinium compound is

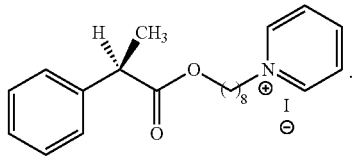

14. The pharmaceutical composition of claim 11, wherein said amphiphilic pyridinium compound is

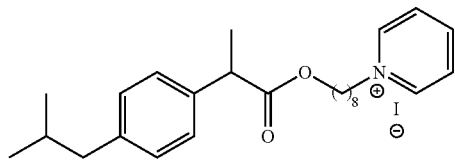

* * * * *